(12) United States Patent
Minamizato et al.

(10) Patent No.: US 10,231,601 B2
(45) Date of Patent: Mar. 19, 2019

(54) MEDICAL APPARATUS FOR ASSOCIATING INDEX INDICATING PRIORITY CORRESPONDING TO LESION OCCURRENCE FREQUENCY WITH POSITION OF INNER WALL OPPOSING IN VISUAL LINE DIRECTION OF ENDOSCOPE THE POSITION BEING ONE AT WHICH IMAGE IS ACQUIRED

(71) Applicant: OLYMPUS CORPORATION, Tokyo (JP)

(72) Inventors: Miho Minamizato, Kurume (JP); Jun Hasegawa, Hino (JP); Syunya Akimoto, Kawasaki (JP)

(73) Assignee: OLYMPUS CORPORATION, Tokyo (JP)

( * ) Notice: Subject to any disclaimer, the term of this patent is extended or adjusted under 35 U.S.C. 154(b) by 38 days.

(21) Appl. No.: 15/385,505

(22) Filed: Dec. 20, 2016

(65) Prior Publication Data

US 2017/0095136 A1    Apr. 6, 2017

Related U.S. Application Data

(63) Continuation of application No. PCT/JP2015/082076, filed on Nov. 16, 2015.

(30) Foreign Application Priority Data

Nov. 17, 2014 (JP) .................................. 2014-232936

(51) Int. Cl.
*A61B 1/06* (2006.01)
*A61B 1/04* (2006.01)
(Continued)

(52) U.S. Cl.
CPC ........ *A61B 1/00009* (2013.01); *A61B 1/0002* (2013.01); *A61B 1/0005* (2013.01);
(Continued)

(58) Field of Classification Search
CPC . A61B 1/00009; A61B 1/0002; A61B 1/0005; A61B 1/04; A61B 1/045;
(Continued)

(56) References Cited

U.S. PATENT DOCUMENTS 8,167,789 B2 *   5/2012   Sato ................... A61B 1/00009
                                                                  600/109
8,509,490 B2 *   8/2013   Takahata ................. G06T 7/292
                                                                  382/107
(Continued)

FOREIGN PATENT DOCUMENTS

EP    2 868 256 A1    5/2015
EP    2 929 831 A1   10/2015
(Continued)

OTHER PUBLICATIONS

International Search Report dated Feb. 9, 2016 received in PCT/JP2015/082076.

*Primary Examiner* — John P Leubecker
*Assistant Examiner* — William Chou
(74) *Attorney, Agent, or Firm* — Scully, Scott, Murphy & Presser, P.C.

(57) ABSTRACT

A medical apparatus includes: an information acquisition section configured to acquire position information and visual line information in an endoscope inserted into a predetermined organ; an image acquisition section configured to acquire an image obtained by observing inside of the predetermined organ from a predetermined viewpoint; an alignment section configured to convert the position information and the visual line information to a coordinate system of a
(Continued)

model of the predetermined organ; a position calculation section configured to calculate position information of an inner wall of the predetermined organ opposing in a visual line direction from the predetermined viewpoint; an index generation section configured to generate an index defined based on a predetermined feature; and an image generation section configured to generate an image in which the index and position information of the inner wall are associated, for the image acquired by the image acquisition section.

14 Claims, 23 Drawing Sheets

(51) Int. Cl.
| | |
|---|---|
| *A61B 1/00* | (2006.01) |
| *G06T 7/292* | (2017.01) |
| *G06T 7/33* | (2017.01) |
| *A61B 1/303* | (2006.01) |
| *A61B 1/307* | (2006.01) |
| *A61B 1/045* | (2006.01) |
| *A61B 5/06* | (2006.01) |
| *G06F 19/00* | (2018.01) |

(52) U.S. Cl.
CPC ............... *A61B 1/04* (2013.01); *A61B 1/045* (2013.01); *A61B 1/303* (2013.01); *A61B 1/307* (2013.01); *A61B 5/066* (2013.01); *G06F 19/00* (2013.01); *G06T 7/292* (2017.01); *G06T 7/344* (2017.01); *G06T 2207/10068* (2013.01)

(58) Field of Classification Search
CPC ....... A61B 1/303; A61B 1/307; A61B 8/0833; A61B 8/0841; A61B 8/085; A61B 2034/2051; A61B 5/065; A61B 5/066; G06F 19/00
USPC ....... 600/102, 103, 109, 117, 118, 137, 139, 600/145, 146, 153, 160, 173, 182
See application file for complete search history.

(56) References Cited

U.S. PATENT DOCUMENTS

| | | | |
|---|---|---|---|
| 2005/0074151 A1* | 4/2005 | Chen | .................. A61B 1/00009 382/128 |
| 2006/0202998 A1* | 9/2006 | Hirakawa | .......... A61B 1/00009 345/501 |
| 2014/0051986 A1* | 2/2014 | Zhao | ...................... A61B 5/066 600/424 |
| 2015/0025316 A1 | 1/2015 | Hasegawa et al. | |
| 2015/0305600 A1 | 10/2015 | Minamizato et al. | |

FOREIGN PATENT DOCUMENTS

| | | |
|---|---|---|
| JP | 2006-61469 A | 3/2006 |
| JP | 2008-173490 A | 7/2008 |
| JP | 5676058 B1 | 2/2015 |
| JP | 5750669 B2 | 7/2015 |
| JP | 5771757 B2 | 9/2015 |
| WO | WO 2014/136579 A1 | 9/2014 |
| WO | WO 2014/148184 A1 | 9/2014 |
| WO | WO 2014/168128 A1 | 10/2014 |

* cited by examiner

FIG. 6A

| REGION | COORDINATE | | | PRIORITY |
|---|---|---|---|---|
| | X | Y | Z | |
| TRIGONE | Xa~Xb | Ya~Yb | Za~Zb | 1 |
| BACK WALL | Xc~Xd | Yc~Yd | Zc~Zd | 2 |
| RIGHT SIDE WALL | ~ | ~ | ~ | 3 |
| LEFT SIDE WALL | ~ | ~ | ~ | 4 |
| FRONT WALL | ~ | ~ | ~ | 5 |
| TOP PORTION | ~ | ~ | ~ | 6 |

FIG. 6B

| REGION | COORDINATE | | | PRIORITY |
|---|---|---|---|---|
| | X | Y | Z | |
| TRIGONE | Xa~Xb | Ya~Yb | Za~Zb | 1 |
| BACK WALL | Xc~Xd | Yc~Yd | Zc~Zd | 2 |
| BACK WALL | Xe~Xf | Ye~Yf | Ze~Zf | 3 |
| RIGHT SIDE WALL | ~ | ~ | ~ | 4 |
| | | | | |

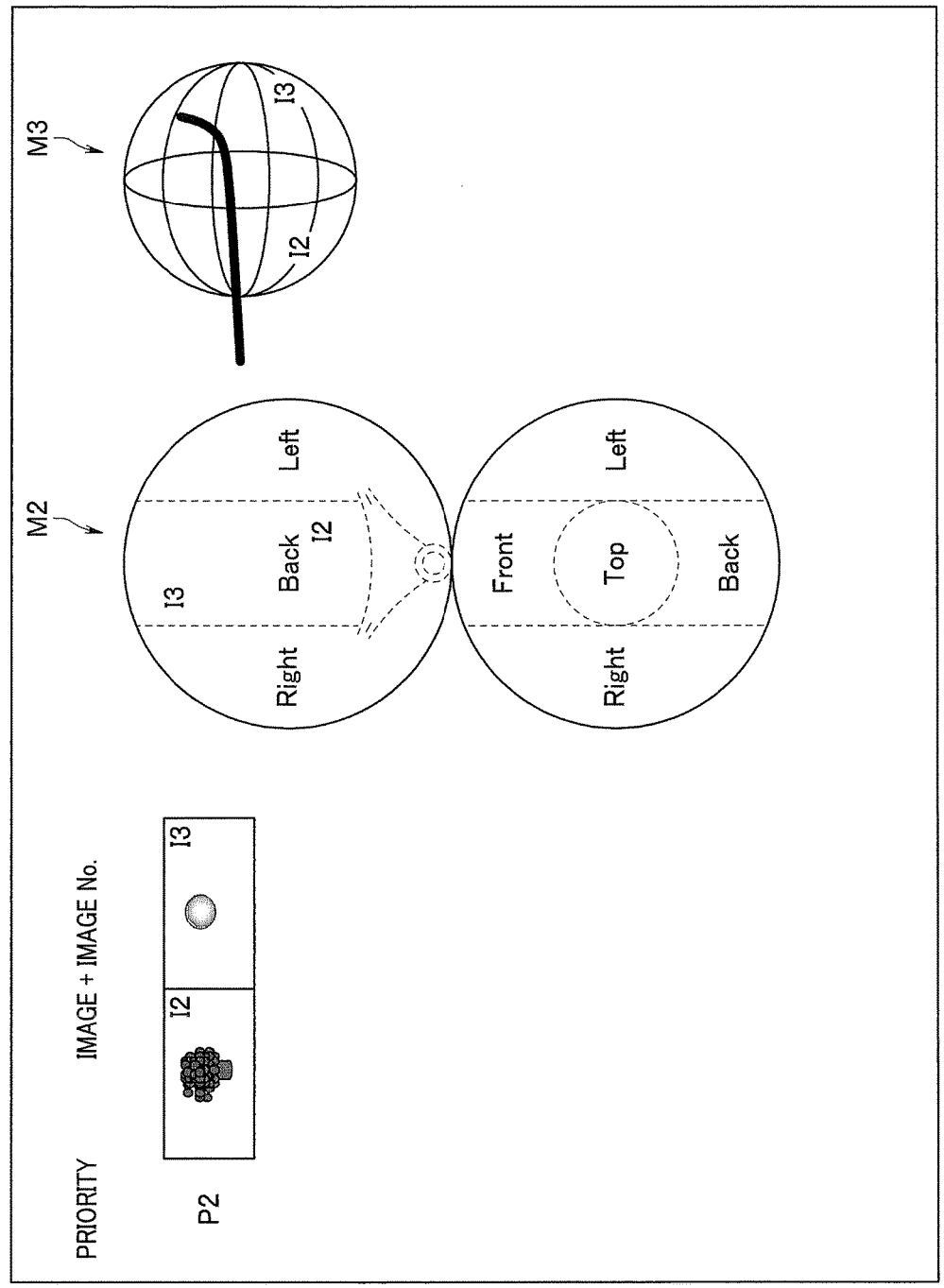

FIG. 10

| PRIORITY | IMAGE | IMAGE No. | Ri/Ti |
|---|---|---|---|
| P1 | | I1 | R1/T1 |
| P2 | | I2 | R2/T2 |
| P3 | | I3 | R3/T3 |
| P4 | | I4 | R4/T4 |
| P5 | | I5 | R5/T5 |
| P6 | | I6 | R6/T6 |
| P7 | | I7 | R7/T7 |
| P8 | | I8 | R8/T8 |
| P9 | | I9 | R9/T9 |

I3

I4 Right | Back I2 | I5 Left

I1

I9 Front

Right I8 | I6 Top | Left I7

Back

FIG. 11

| PRIORITY | IMAGE | IMAGE No. |
|---|---|---|
| P1 | | I3 |
| P2 | | I4 |
| P3 | | I7 |
| P4 | | I6 |
| P5 | | I9 |
| P6 | | I2 |
| P7 | | I5 |
| P8 | | I1 |
| P9 | | I8 |

I8

I2 Right | Back I4 | I7 Left

I3

I6 Front

Right I5 | I9 Top | Left I1

Back

B1 TRIGONE
B2, B3 OUTSIDE OF URETERAL ORIFICES ON BOTH SIDES
B4, B5 BOTH SIDE WALLS
B6 BACK WALL
B7 TOP PORTION
B8 NECK

FIG. 17

| RELEASE NUMBER j | REGION | TEMPORARY PRIORITY Pi(Lmm) | PRIORITY |
|---|---|---|---|
| 1 | TRIGONE | P1(20mm) | P2(P1-2) |
| 2 | BACK WALL | P2(25mm) | P5(P2-3) |
| 3 | BACK WALL | P2(15mm) | P3(P2-1) |
| 4 | BACK WALL | P2(20mm) | P4(P2-2) |
| 5 | TRIGONE | P1(15mm) | P1(P1-1) |

MEDICAL APPARATUS FOR ASSOCIATING INDEX INDICATING PRIORITY CORRESPONDING TO LESION OCCURRENCE FREQUENCY WITH POSITION OF INNER WALL OPPOSING IN VISUAL LINE DIRECTION OF ENDOSCOPE THE POSITION BEING ONE AT WHICH IMAGE IS ACQUIRED

CROSS REFERENCE TO RELATED APPLICATION

This application is a continuation application of PCT/JP2015/082076 filed on Nov. 16, 2015 and claims benefit of Japanese Application No. 2014-232936 filed in Japan on Nov. 17, 2014, the entire contents of which are incorporated herein by this reference.

BACKGROUND OF THE INVENTION

1. Field of the Invention

The present invention relates to a medical apparatus inserted into a subject and configured to acquire an image.

2. Description of the Related Art

In recent years, an endoscope apparatus including an endoscope as a medical apparatus inserted into a subject and configured to observe inside of the subject and perform a treatment by using a treatment instrument or the like has been widely used. There is an apparatus configured to use the endoscope to observe inside of a predetermined luminal organ to be observed (or examined) and record lesion images when a lesion part is discovered. The apparatus links locations of the lesion images with the lesion images and records the lesion images.

For example, Japanese Patent Application Laid-Open Publication No. 2006-61469 as a first conventional example discloses an image display apparatus including a display section configured to display a series of images in which a desired object is photographed in chronological order. The image display apparatus includes a control section configured to control the display section to display a time bar provided with a time scale indicating image pickup periods of the series of images and to display an index indicating a position on the time scale corresponding to image pickup time of a desired image selected from the series of images.

Japanese Patent Application Laid-Open Publication No. 2008-173490 as a second conventional example discloses a configuration including: a display section configured to display a series of images in which inside of a subject is photographed in chronological order and to display a time bar indicating image pickup periods of the series of images by using different colors for respective sites of the inside of the subject; and a control section configured to perform control of discriminating respective sites in the subject displayed on the series of images and displaying respective alternate colors corresponding to the respective sites in the subject in respective regions of the time bar temporally corresponding to image groups of the respective discriminated sites in the subject.

SUMMARY OF THE INVENTION

An aspect of the present invention provides a medical apparatus including: an information acquisition section configured to acquire position information and visual line information in an endoscope inserted into a predetermined organ; an image acquisition section configured to acquire an image obtained by observing inside of the predetermined organ from a predetermined viewpoint; an alignment section configured to convert the position information and the visual line information acquired by the information acquisition section to a coordinate system of a model of the predetermined organ; a position calculation section configured to calculate position information of an inner wall of the predetermined organ opposing in a visual line direction from the predetermined viewpoint based on the position information and the visual line information converted to the coordinate system of the model of the predetermined organ by the alignment section; an index generation section configured to generate an index defined based on the image acquired by the image acquisition section or a predetermined feature in the inner wall; and an image generation section configured to generate an image in which the index generated by the index generation section and position information of the inner wall are associated, for the image acquired by the image acquisition section.

BRIEF DESCRIPTION OF THE DRAWINGS

FIG. 6A is a diagram showing a tabular form of content of a table recording information in which regions with higher lesion occurrence frequencies are provided with higher priorities;

FIG. 6B is a diagram showing a tabular form of part of content of a table recording information in which regions in different three-dimensional positions are provided with different priorities even in regions with a same name;

FIG. 9D is a diagram showing an association image provided with indices on the 2D model image and on the 3D image (modification of display of FIG. 9B, corresponding only to the priority P2);

FIG. 10 is a diagram showing an association image when a chronological order is selected as an item for generating the indices;

FIG. 11 is a diagram showing an association image when an order of size of lesion is selected as an item for generating the indices;

FIG. 17 is an explanatory diagram showing a tabular form of content of the process of FIG. 16.

DETAILED DESCRIPTION OF THE PREFERRED EMBODIMENT

Hereinafter, an embodiment of the present invention will be described with reference to the drawings.

First Embodiment

Figure 1:
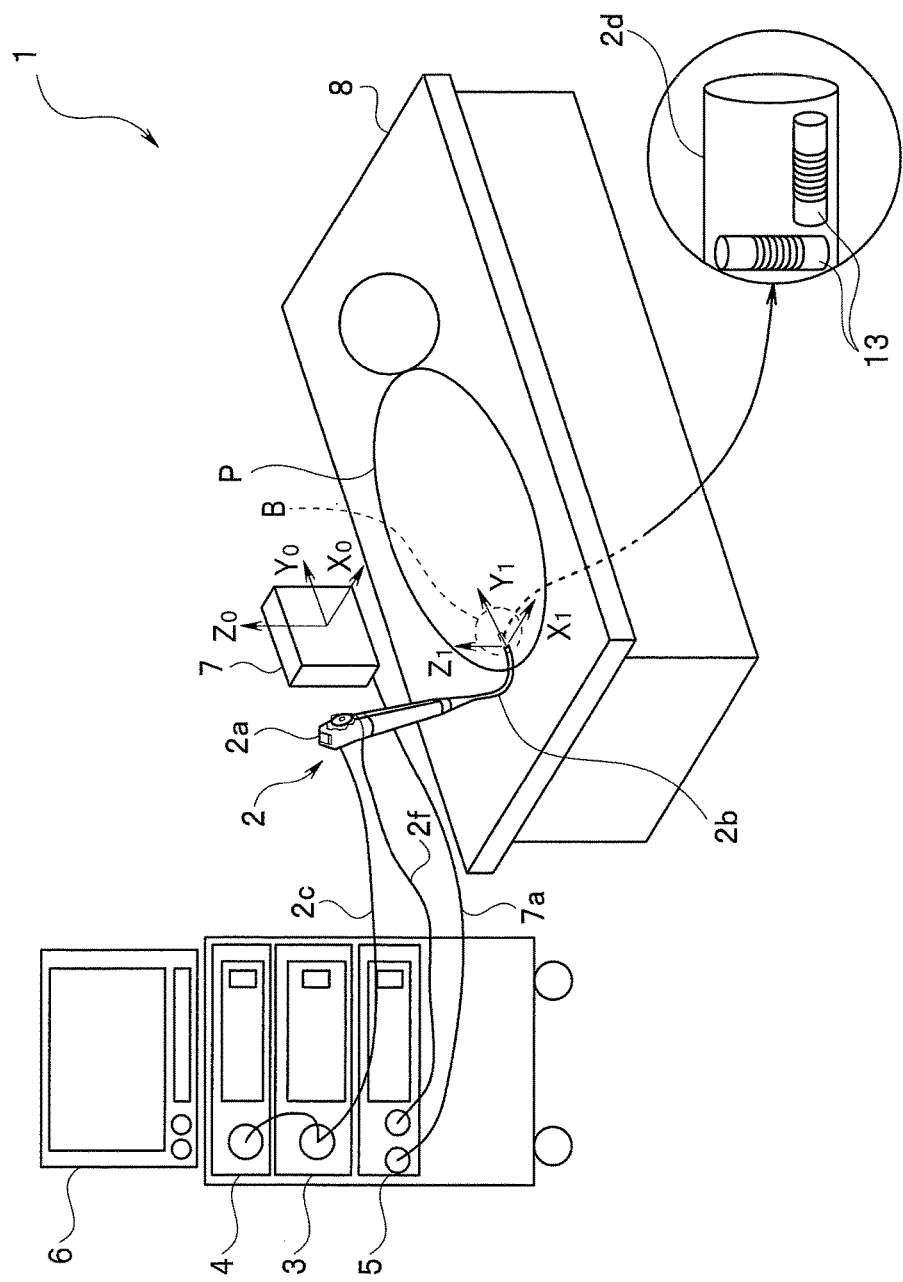
FIG. 1 is a diagram showing an overall configuration of a medical apparatus according to a first embodiment of the present invention.

As shown in FIG. 1, a medical apparatus 1 of a first embodiment of the present invention includes: an endoscope 2 configured to observe (or examine) inside of a predetermined luminal organ (bladder B in a specific example) inside of a patient P as a subject; a light source apparatus 3; a processor 4; an image processing apparatus 5; a monitor 6; and a magnetic field generation apparatus 7. The medical apparatus 1 has a function for observation in two observation modes, normal light observation and special light observation. A surgeon as a user of the medical apparatus 1 performs endoscopy of the inside of the bladder B as a predetermined luminal organ (also simply called a luminal organ or an organ) in the patient P laid on the back on a bed 8, for example.

The endoscope 2 includes an operation portion 2a, a flexible insertion portion 2b, and a universal cable 2c. The endoscope 2 is configured by, for example, an endoscope for bladder examination.

Figure 2:
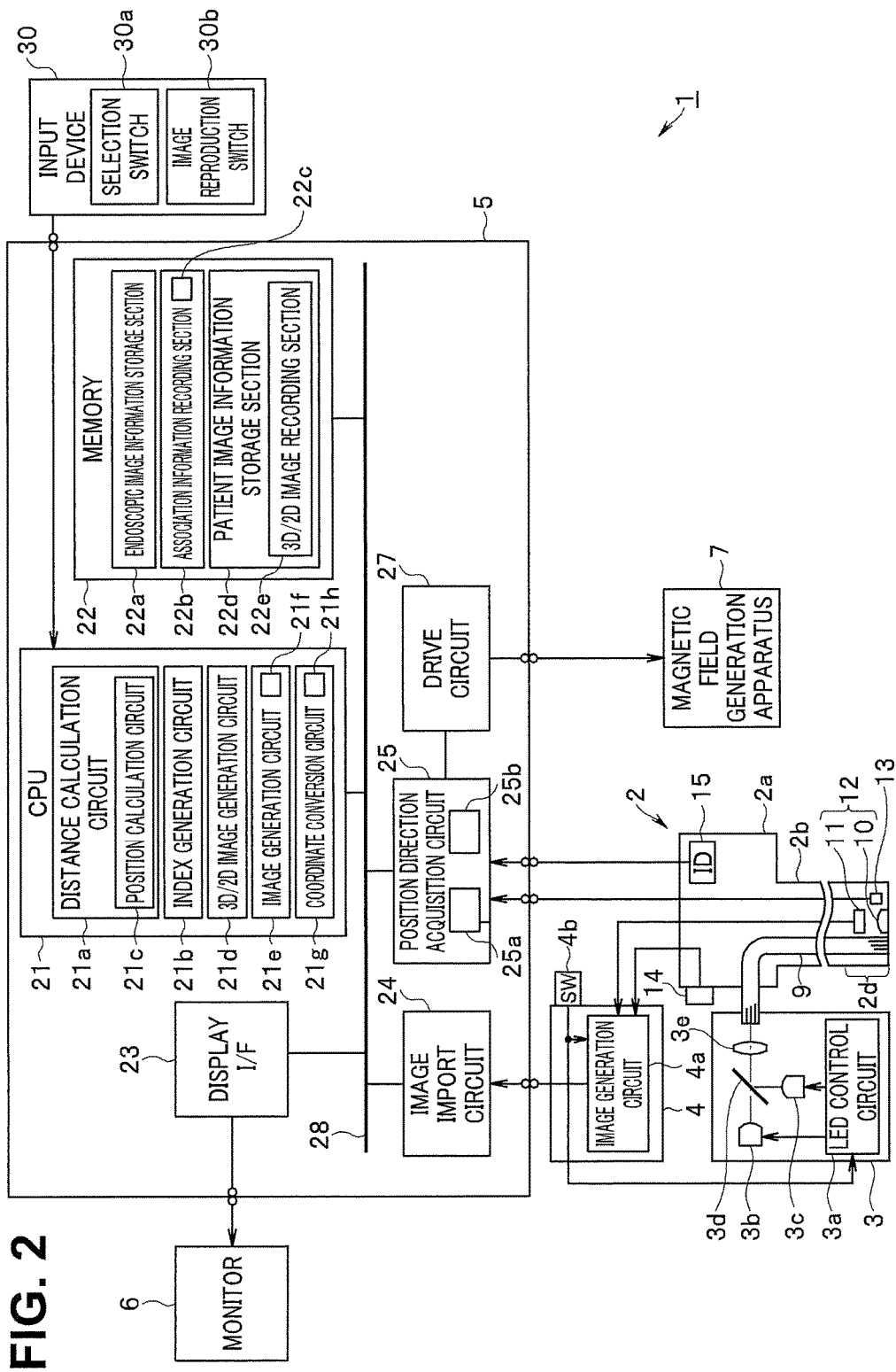
FIG. 2 is a block diagram showing a configuration of an image processing apparatus and the like in FIG. 1.

Furthermore, a light guide 9 as shown in FIG. 2 is inserted into the universal cable 2c. The endoscope 2 emits illumination light from the light source apparatus 3, from an illumination window of a distal end portion 2d of the insertion portion 2b through the light guide 9 and illuminates the inside of the predetermined luminal organ (the bladder B as the predetermined luminal organ) in the subject into which the distal end portion 2d of the insertion portion 2b is inserted.

As shown in FIG. 2, the distal end portion 2d of the insertion portion 2b is provided with: an objective optical system 10 configured to receive light from the subject to form an optical image; and an image pickup device 11 including an image pickup surface at an image formation position of the optical image and configured to photoelectrically convert the optical image formed on the image pickup surface to output an image pickup signal. The image pickup device 11 picks up an image of an inner wall of the bladder B illuminated by the illumination light of the light source apparatus 3. Therefore, the objective optical system 10 and the image pickup device 11 form an image pickup section (or an image pickup apparatus) 12 configured to pick up an image of the inside of a luminal organ. The image pickup signal obtained by the image pickup device 11 is inputted to the processor 4 configured to generate a photographed image of the inside of the bladder B as a luminal organ, through a signal line in the universal cable 2c. An image generation circuit 4a in the processor 4 applies an image generation process to the image pickup signal, and an endoscopic image as a photographed image obtained by picking up an image of the inside of the bladder B is generated.

In the present embodiment, the image generation circuit 4a in the processor 4 converts the optical image of the subject formed on the image pickup surface of the image pickup device 11 of the image pickup section 12 mounted on the distal end portion 2d to an electrical image pickup signal to generate a photographed image corresponding to the optical image, and the generated photographed image is displayed in an endoscopic image display area in the monitor 6. In the configuration of FIG. 2, the endoscopic image generated by the image generation circuit 4a is superimposed on or synthesized with another image generated by the image processing apparatus 5 and displayed in the endoscopic image display area of the monitor 6 through the image processing apparatus 5.

The position of the image pickup section 12 that picks up an image of the inner wall of the bladder B and the image pickup direction of the image pickup (optical axis direction of the objective optical system 10) is the position of the viewpoint and the visual line direction in generating the photographed image.

The processor 4 includes a change-over switch 4b for switching the observation mode. An observation mode signal designated by the change-over switch 4b is inputted to the image generation circuit 4a, and the image generation circuit 4a generates an endoscopic image according to the observation mode designated by the change-over switch 4b. More specifically, when the normal light observation mode is designated, a normal light observation image picked up under the illumination of normal light (white light as normal light) is generated. When the special light observation mode is designated, a special light observation image (narrow band light observation image in a narrower sense) is generated.

The observation mode signal based on the change-over switch 4b is inputted to an LED control circuit 3a of the light source apparatus 3, and the LED control circuit 3a performs control to generate illumination light according to the observation mode.

When the normal light observation mode is designated by the change-over switch 4b, the LED control circuit 3a controls and causes a white LED 3b as a light source for normal light observation mode to emit light. When the special light observation mode is designated, the LED control circuit 3a controls and causes a narrow-band blue LED 3c as a light source for special light observation mode to emit light.

When the narrow-band blue LED 3c emits light, the narrow-band blue light is selectively reflected by a dichroic mirror 3d arranged at an angle of 45 degrees on an optical path of the advancing light. The light is condensed by a condenser lens 3e and is incident on a proximal end of the light guide 9. The narrow-band blue illumination light incident on the proximal end of the light guide 9 is transmitted by the light guide 9 and emitted from an illumination window to which a distal end of the light guide 9 is attached. Illumination for special light observation mode (illumination for narrow band light observation mode in a narrower sense) is performed.

When the white LED 3b emits light, most of the white light excluding the narrow-band blue light is selectively transmitted by the dichroic mirror 3d arranged on an optical path of the white light. The light is condensed by the condenser lens 3e and is incident on the proximal end of the light guide 9. The white illumination light excluding the narrow-band blue light incident on the proximal end of the light guide 9 is transmitted by the light guide 9 and emitted from the illumination window to which the distal end of the light guide 9 is attached. Illumination for normal light observation mode is performed.

The endoscopic image generated by the processor 4 (the image generation circuit 4a of the processor 4) is outputted to the monitor 6, and a live endoscopic image is displayed on the monitor 6. The surgeon who conducts the examination can insert the distal end portion 2d of the insertion portion 2b from the urethra of the patient P and observe the inside of the bladder B (indicated by a dotted line in FIG. 1) of the patient P.

A magnetic sensor 13 as a position sensor is further arranged on the distal end portion 2d of the insertion portion 2b. More specifically, the magnetic sensor 13 is provided near the objective optical system 10 and the image pickup device 11 included in the image pickup section 12 of the distal end portion 2d as shown in FIG. 2. The magnetic sensor 13 is used to detect a three-dimensional position (simply, position) as a viewpoint of the image pickup section 12 on the distal end portion 2d and a visual line direction at the position.

In the endoscope 2 shown in FIG. 2, an optical axis direction of the objective optical system 10 included in the image pickup section 12 mounted on the distal end portion 2d is parallel to an axis direction of the distal end portion 2d. Therefore, the position and the visual line direction of the image pickup section 12 can be approximated as a position and an axis direction (simply, direction) of the distal end portion 2d.

Note that the present embodiment is not limited to the case of the endoscope 2 in which the objective optical system 10 arranged on the distal end portion 2d as shown in FIG. 2 forms an optical image of the subject on the image pickup surface of the image pickup device 11 arranged on the distal end portion 2d. The present embodiment can also be applied to a case of an endoscope in which an optical image formed by the objective optical system 10 arranged on the distal end portion 2d is transmitted to a back (proximal end) side of the insertion portion 2b, and an image pickup device arranged on the proximal end side of the insertion portion 2b picks up an image.

It is more appropriate to use the position of the viewpoint (and the visual line direction) of the objective optical system 10 (arranged on the distal end portion 2d) for the expression including this case than to use the expression of the position of the viewpoint (and the visual line direction) of the image pickup section. Therefore, the position of the viewpoint and the visual line direction may be mainly used below as the position of the viewpoint and the visual line direction of the objective optical system 10, or the position (of the objective optical system 10, the distal end portion 2d, or the distal end) and the direction may be used instead of the position of the viewpoint and the visual line direction as approximate expression.

As shown in an enlarged view of FIG. 1, the magnetic sensor 13 includes, for example, two coils 2e. The magnetic sensor 13 is a sensor configured to detect the position and the direction of the distal end portion 2d. A signal line 2f of the magnetic sensor 13 is extended from the endoscope 2 and connected to the image processing apparatus 5 (a position direction acquisition circuit 25 in the image processing apparatus 5).

The magnetic field generation apparatus 7 generates a magnetic field at an already-known predetermined position, and the magnetic sensor 13 detects the magnetic field generated by the magnetic field generation apparatus 7. A detection signal of the magnetic field is inputted from the endoscope 2 to the image processing apparatus 5 (the position direction acquisition circuit 25 in the image processing apparatus 5) through the signal line 2f.

The position direction acquisition circuit 25 has a function of an information acquisition section (or an information acquisition circuit) 25a configured to acquire position information of the viewpoint (also called viewpoint position information) and visual line direction information as information of the position of the viewpoint and the visual line direction of the objective optical system 10 arranged on the distal end portion 2d, from an amplitude and a phase of the inputted detection signal. Note that in the present embodiment, the luminal organ to be observed is the inner wall of the bladder B, and the bladder B can be approximated by a spherical three-dimensional (3D) image as described later. That is, the bladder B is approximated by a 3D image M3 (FIG. 4) expressed by a sphere.

A release switch (or a release button) 14 is provided on the operation portion 2a of the endoscope 2. The release switch 14 is a switch pressed by the user, such as a surgeon, to record the endoscopic image. When the release switch 14 is pressed, a release switch operation signal is inputted to the processor 4, and the processor 4 generates a release signal and outputs the release signal to the image processing apparatus 5.

The endoscopic image when the release switch 14 is pressed is recorded in a memory 22 inside of the image processing apparatus 5 through an image import circuit 24 forming an image acquisition section described later in the image processing apparatus 5. Note that it may be defined that the image import circuit 24 and the memory 22 form the image acquisition section.

In the present embodiment, as described later, when the endoscopic image after the press of the release switch 14 is recorded, an index provided with a priority reflecting, for example, a predetermined feature set by the surgeon, a set predetermined feature, or a predetermined feature selected from a plurality of predetermined features is recorded in association with position information (near the center on the inner wall upon recording) of the endoscopic image to be recorded. In this way, when recorded endoscopic images are to be checked, a plurality of endoscopic images with high priorities indicating the order of priority can be prioritized and checked (reproduction can be displayed).

The endoscope 2 also includes an ID generation section (simply abbreviated as ID in FIG. 2) 15 configured by a ROM (read only memory) or the like for generating identification information (abbreviated as ID) specific to each endoscope 2. The ID generated by the ID generation section 15 is inputted to the image processing apparatus 5 (the position direction acquisition circuit 25 in the image processing apparatus 5) through the processor 4.

As shown in FIG. 2, the ID may be inputted to the image processing apparatus 5 (the position direction acquisition circuit 25 in the image processing apparatus 5) without going through the processor 4. The position direction acquisition circuit 25 has a function of an image pickup information acquisition section (or an image pickup information acquisition circuit) 25b configured to acquire, from the ID, image pickup information when the image pickup section 12 picks up an image, the image pickup information including a focal length of the objective optical system 10, the number of pixels of the image pickup device 11 configured to pick up the optical image taken by the objective optical system 10, a size of the pixel, and the like. The acquired image pickup information may be used to generate the index described later.

The image processing apparatus 5 includes a central processing unit (hereinafter, called a CPU) 21, the memory 22, a display interface (hereinafter, abbreviated as a display I/F) 23, the image import circuit 24, the position direction acquisition circuit 25, and a drive circuit 27. The CPU 21, the memory 22, the display I/F 23, the image import circuit 24, and the position direction acquisition circuit 25 are connected to each other through a bus 28. The medical apparatus 1 also includes an input device 30 for the user to perform input, to the image processing apparatus 5, for inputting or selecting various pieces of information.

The CPU 21 configures a control section (or a control circuit) configured to control processes of each section in the image processing apparatus 5 and includes: a position calculation circuit 21c forming a position calculation section configured to use the position information of the viewpoint, the visual line direction information, and the image pickup information acquired by the position direction acquisition circuit 25 to calculate a viewpoint of the objective optical system 10 arranged on the distal end portion 2d and a position (or position information including the position) intersecting the inner wall (surface) of the bladder B as a luminal organ in (at least) the visual line direction from the viewpoint; and an index generation circuit 21b forming an index generation section configured to generate an index defined (or determined) based on an endoscopic image generated by the image generation circuit 4a and acquired (recorded) in the memory 22 through the image import circuit 24 or based on a predetermined feature in the inner wall of the bladder B.

In other words, the index generation circuit 21b generates an index reflecting the predetermined feature. In the present embodiment, as described later, an arbitrary item can be selected from items for generating a plurality of types of indices reflecting different types of features to generate an index reflecting the feature corresponding to the selected item.

The position calculation circuit 21c includes a distance calculation circuit 21a configured to calculate a distance between the position (or the position information including the position) on the inner wall calculated by the position calculation circuit 21c and the viewpoint.

The CPU 21 further includes: a 3D/2D image generation circuit 21d configured to generate the 3D image (or a 3D model image as an approximate image of the 3D image) M3 of the luminal organ and a 2D model image M2 (a bladder schema, or simply called a schema) as a model image of a two-dimensional (2D) image obtained by developing the luminal organ; and an image generation circuit 21e forming an image generation section configured to generate, on the 3D image M3 or the 2D model image M2, an image (also called an association image) associating the index with the position (information) on the inner wall of the luminal organ when the index is generated.

The image generation circuit 21e has a function of an association circuit 21f forming an association section configured to associate an index generated based on the predetermined feature or the like in the inner wall of the bladder B with the endoscopic image to be recorded (or recorded) by the release operation acquired through the image import circuit 24. Note that the association circuit 21f may be provided outside of the image generation circuit 21e, or the association circuit 21f may include the image generation circuit 21e. The image generation circuit 21e in FIG. 2 may include the index generation circuit 21b, or conversely, the index generation circuit 21b may include the image generation circuit 21e. The index generation circuit 21b may have the function of the association circuit 21f.

Figure 3A:
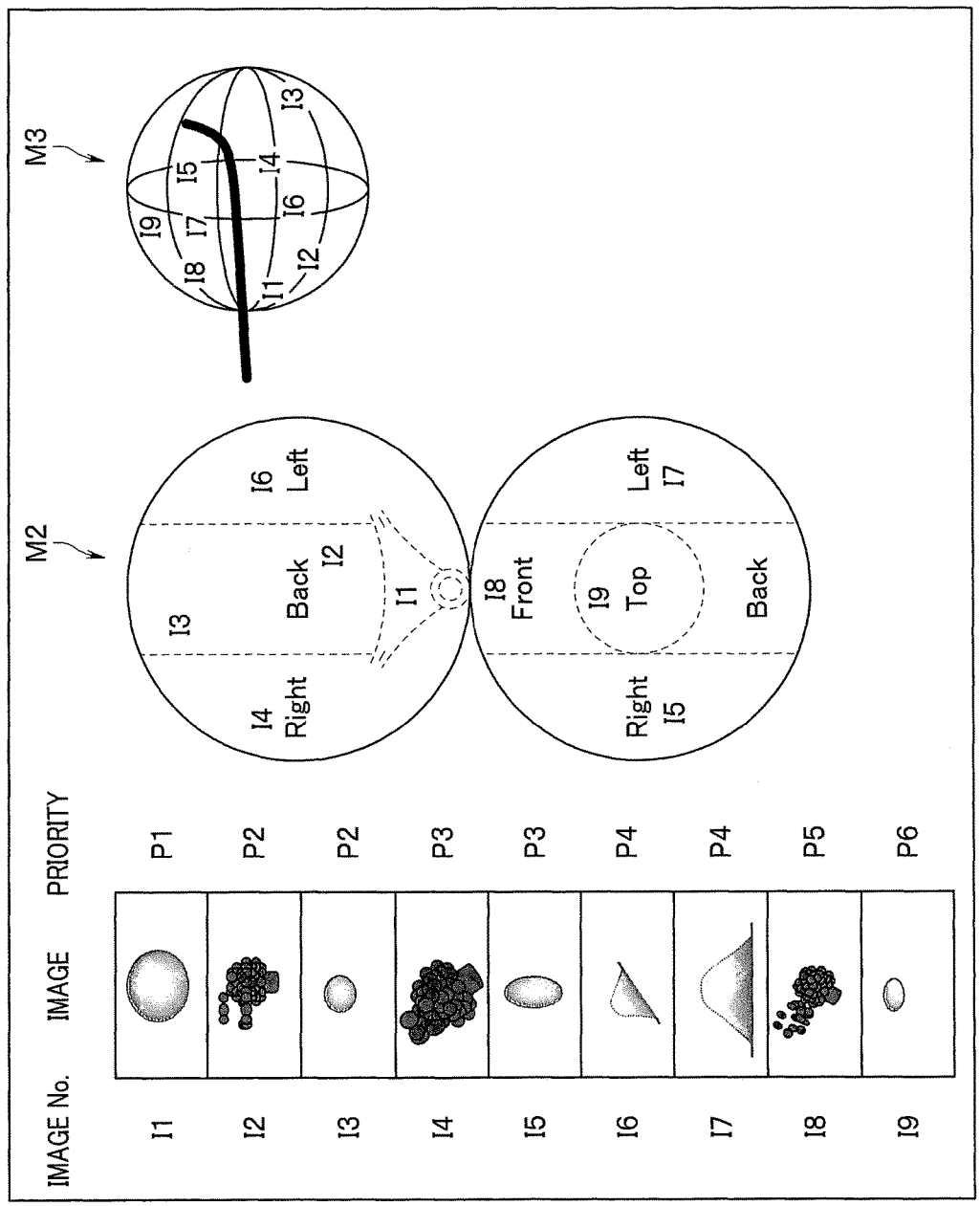
FIG. 3A is a diagram showing an association image provided with indices on a 2D model image and on a 3D image.

The image generation circuit 21e generates an (association) image on the 2D model image M2 and on the 3D image as shown for example in FIG. 3A and displays the image on the monitor 6.

A leftmost line in FIG. 3A schematically shows endoscopic images (thumbnail images of the endoscopic images) Ii (i=1, 2, . . . , 9) recorded in the memory 22 in a state that priorities Pi (the smaller the order i, the higher the priority) forming the indices reflecting the predetermined feature are provided. In the 2D model image M2 (bladder schema) at the center, the positions on the inner wall of the bladder B where the recorded endoscopic images are picked up are illustrated on the bladder schema, and the endoscopic images (thumbnail images of the endoscopic images) Ii are provided. Note that Ii will also be called an image No. of the endoscopic image (thumbnail image of the endoscopic image).

Figure 3B:
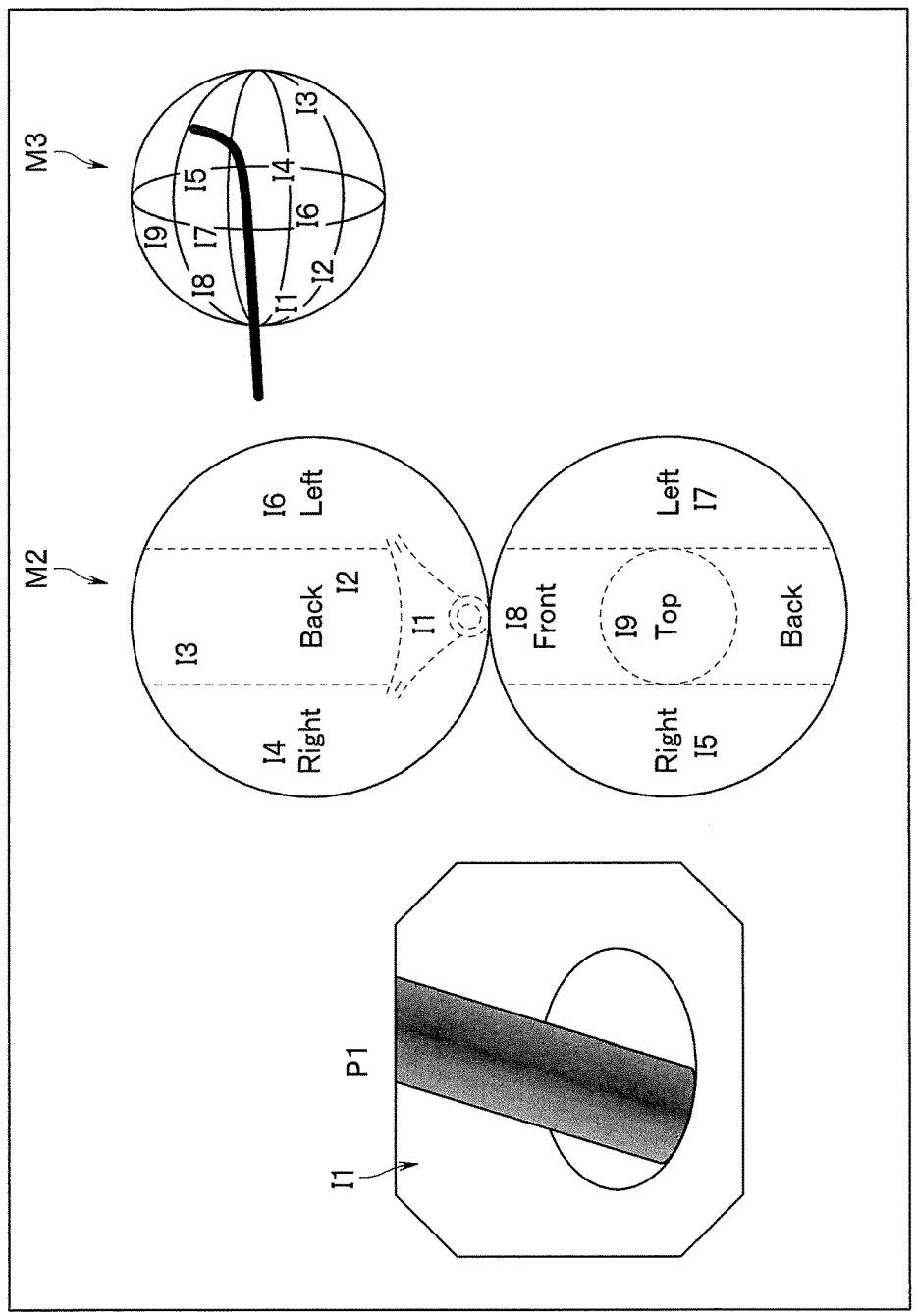
FIG. 3B is a diagram showing a situation in which an endoscopic image with a highest priority is displayed from FIG. 3A.
Figure 3C:
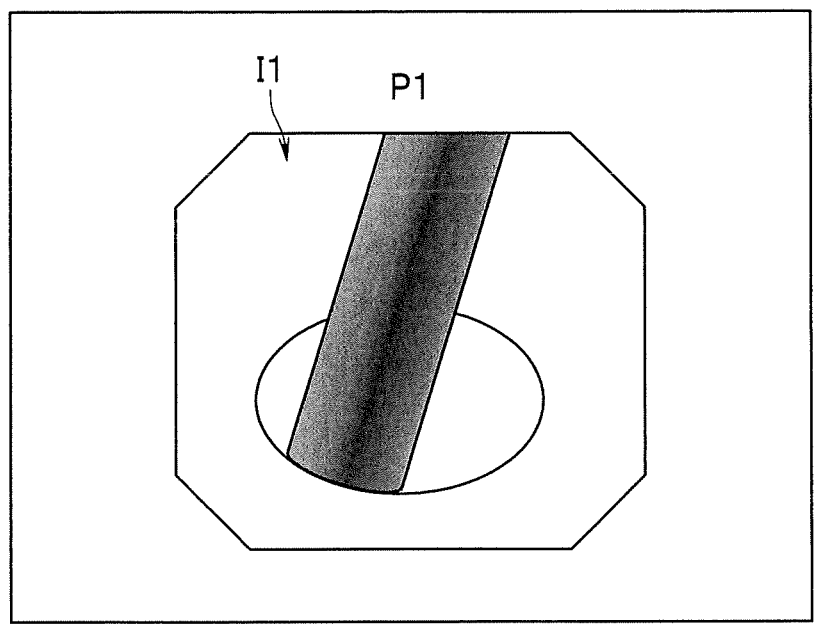
FIG. 3C is a diagram showing a situation in which only the endoscopic image with the highest priority is displayed.

In the rightmost 3D image of FIG. 3A, the positions on the inner wall where the recorded endoscopic images are picked up are illustrated on the 3D image, and the endoscopic images (thumbnail images of the endoscopic images) Ii are provided, as in the case on the bladder schema at the center. After the images of FIG. 3A are displayed on the monitor 6, the endoscopic images are sequentially displayed on the monitor 6 in descending order of priority. FIGS. 3B and 3C show a situation of displaying an endoscopic image I1 of a priority P1 with a highest priority. Note that the images of FIG. 3B or FIG. 3C may be displayed without displaying the images of FIG. 3A.

The CPU 21 also has a function of a coordinate conversion circuit 21g configured to convert a first coordinate system $(X_0Y_0Z_0)$ (see FIG. 1) as a coordinate system on the basis of the magnetic field generation apparatus 7 to an intermediate coordinate system $(X_1Y_1Z_1)$ (see FIG. 1) on the basis of an entrance of the bladder when the CPU 21 acquires the position information of the viewpoint and the visual line direction information acquired by the position direction acquisition circuit 25.

Note that as described later, the coordinate conversion circuit 21g also has a function of converting the intermediate coordinate system $(X_1Y_1Z_1)$ to a second coordinate system $(X_2Y_2Z_2)$. Therefore, the coordinate conversion circuit 21g has a function of converting the first coordinate system $(X_0Y_0Z_0)$ to the second coordinate system $(X_2Y_2Z_2)$. When the coordinates are converted between two coordinate systems, the coordinate conversion circuit 21g also has a function of an alignment circuit 21h forming an alignment section configured to execute an alignment process of determining transform coefficients, transformation matrices, and the like at the positions already known in both coordinate systems.

The coordinate conversion circuit 21g determines, for example, a position (PR in FIG. 4) and a direction of the entrance of the bladder B as a reference position and a reference direction of the alignment and converts the position direction information of the position direction acquisition circuit 25 to position direction information of the intermediate coordinate system $(X_1Y_1Z_1)$ on the basis of the entrance of the bladder B according to the following equation (1) and equation (2).

$$P_1 = R_{01}P_0 + M_{01} \quad \text{equation (1)}$$

$$V_1 = R_{01}V_0 \quad (2)$$

Here, $P_0$ and $V_0$ respectively denote a position (written in vector) and a direction vector (with a size of 1) in the first coordinate system $(X_0Y_0Z_0)$ that is a coordinate system on the basis of the magnetic field generation apparatus 7. $R_{01}$ denotes a rotation matrix indicated by the following equation (3), and $M_{01}$ denotes a translation matrix indicated by the following equation (4).

[Expression 3]

$$R_{01} = \begin{pmatrix} r_{00} & r_{01} & r_{02} \\ r_{10} & r_{11} & r_{12} \\ r_{20} & r_{21} & r_{22} \end{pmatrix} \quad \text{equation (3)}$$

[Expression 4]

$$M_{01} = \begin{pmatrix} m_{x01} \\ m_{y01} \\ m_{z01} \end{pmatrix} \quad \text{equation (4)}$$

Therefore, a point $(x_0, y_0, z_0)$ on the first coordinate system $(X_0Y_0Z_0)$ is converted to a point $(x_1, y_1, z_1)$ on the intermediate coordinate system $(X_1Y_1Z_1)$ as indicated by the following equation (5).

[Expression 5]

$$\begin{pmatrix} x_1 \\ y_1 \\ z_1 \end{pmatrix} = \begin{pmatrix} r_{00} & r_{01} & r_{02} \\ r_{10} & r_{11} & r_{12} \\ r_{20} & r_{21} & r_{22} \end{pmatrix} \begin{pmatrix} x_0 \\ y_0 \\ z_0 \end{pmatrix} + \begin{pmatrix} m_{x01} \\ m_{y01} \\ m_{z01} \end{pmatrix} \quad \text{equation (5)}$$

Assuming that the vector of the position and the direction acquired by the position direction acquisition circuit 25 when the insertion of the distal end portion 2d (the objective optical system 10 of the distal end portion 2d) of the endoscope 2 into the bladder B is detected is $P'_0$, $V'_0$, the translation matrix $M_{01}$ can be obtained by the following equation (6).

$$M_{01} = -P'_0 \quad \text{equation (6)}$$

The rotation matrix $R_{01}$ is obtained to satisfy the following conditions. The conditions satisfying the rotation matrix $R_{01}$ include: the $Z_1$ axis is parallel to a gravity direction; $V'_0$ is projected on an $X_1Y_1$ plane perpendicular to the $Z_1$ axis, and the projected vector direction is the $Y_1$ axis; and a vector perpendicular to an $Y_1Z_1$ plane is the $X_1$ axis.

Figure 4:
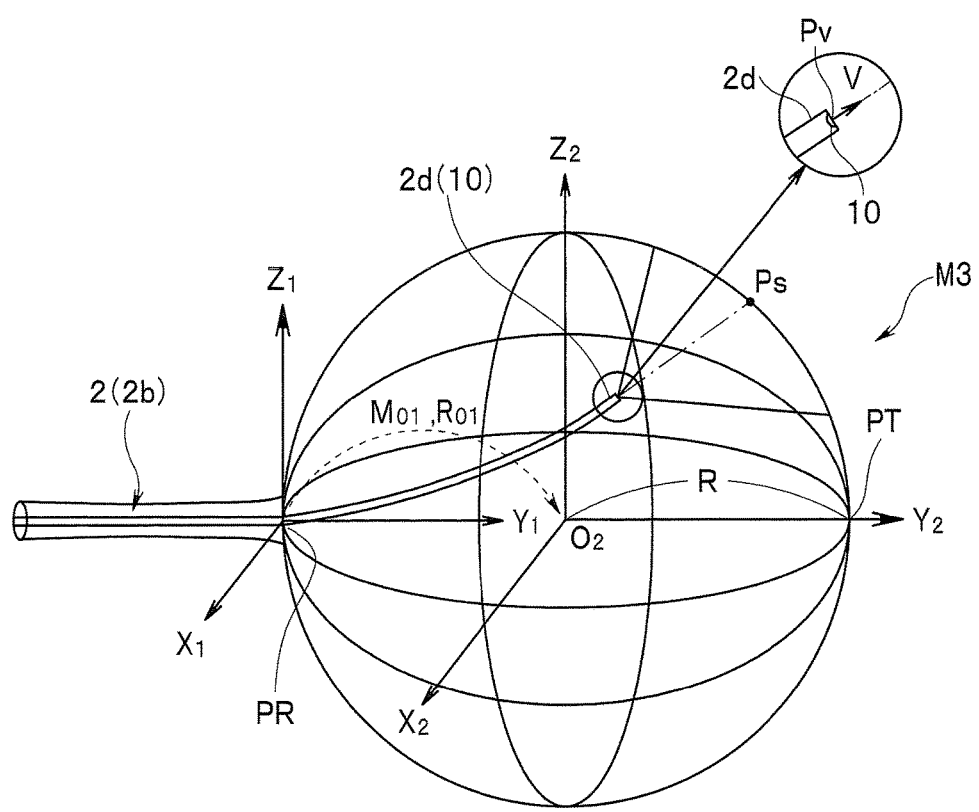
FIG. 4 is a diagram showing a second coordinate system and the like set in the 3D image in which a bladder is approximated by a sphere.

The coordinate conversion circuit 21g further converts the position vector and the direction vector of the intermediate coordinate system $(X_1Y_1Z_1)$ to a position vector and a direction vector in the second coordinate system $(X_2Y_2Z_2)$ on the basis of a center $O_2$ of the spherical 3D image M3 according to the following equation (7) and equation (8). FIG. 4 is a diagram for describing a relationship between the intermediate coordinate system $(X_1Y_1Z_1)$ and the second coordinate system $(X_2Y_2Z_2)$.

$$P_2 = R_{12}P_1 + M_{02} \quad (7)$$

$$V_2 = R_{12}V_1 \quad (8)$$

Here, $P_1$ and $V_1$ respectively denote a position (vector) and a direction vector at an arbitrary position in the intermediate coordinate system $(X_1Y_1Z_1)$, and $P_2$ and $V_2$ respectively denote a position vector and a direction vector after the conversion to the second coordinate system $(X_2Y_2Z_2)$.

When $P_0$ and $V_0$ are set to the position (vector) indicating the position of the viewpoint of the objective optical system 10 of the distal end portion 2d and the direction vector in the visual line direction calculated from the position direction acquisition circuit 25, $P_0$ and $V_0$ are converted to $P_1$ and $V_1$, and $P_1$ and $V_1$ are further converted to $P_2$ and $V_2$.

That is, when $P_0$ and $V_0$ are acquired as the position of the viewpoint and the direction vector in the visual line direction, the corresponding $P_2$ and $V_2$ are a position vector (also indicated by Pv) of a viewpoint Pv of the objective optical system 10 and a direction vector (also indicated by V) in a visual line direction V in the second coordinate system $(X_2Y_2Z_2)$. $R_{12}$ denotes a rotation matrix indicated by the following equation (9), and $M_{02}$ denotes a translation matrix indicated by the following equation (10).

[Expression 9]

$$R_{12} = \begin{pmatrix} r'_{00} & r'_{01} & r'_{02} \\ r'_{10} & r'_{11} & r'_{12} \\ r'_{20} & r'_{21} & r'_{22} \end{pmatrix} \quad \text{equation (9)}$$

[Expression 10]

$$M_{02} = \begin{pmatrix} m_{x12} \\ m_{y12} \\ m_{z12} \end{pmatrix} \quad \text{equation (10)}$$

Therefore, the point $(x_1, y_1, z_1)$ on the intermediate coordinate system $(X_1Y_1Z_1)$ is converted to a point $(x_2, y_2, z_2)$ on the second coordinate system $(X_2Y_2Z_2)$ as shown in the following equation (11).

[Expression 11]

$$\begin{pmatrix} x_2 \\ y_2 \\ z_2 \end{pmatrix} = \begin{pmatrix} r'_{00} & r'_{01} & r'_{02} \\ r'_{10} & r'_{11} & r'_{12} \\ r'_{20} & r'_{21} & r'_{22} \end{pmatrix} \begin{pmatrix} x_1 \\ y_1 \\ z_1 \end{pmatrix} + \begin{pmatrix} m_{x12} \\ m_{y12} \\ m_{z12} \end{pmatrix} \quad \text{equation (11)}$$

When the $X_1Y_1Z_1$ coordinate system is moved by $R_2$ in the $Y_1$ axis direction, the translation $M_{12}$ and the rotation $R_{12}$ are as in equation (12) and equation (13), respectively.

[Expression 12]

$$M_{12} = \begin{pmatrix} m_{x12} \\ m_{y12} \\ m_{z12} \end{pmatrix} = \begin{pmatrix} 0 \\ -R_2 \\ 0 \end{pmatrix} \quad \text{equation (12)}$$

[Expression 13]

$$R_{12} = \begin{pmatrix} r'_{00} & r'_{01} & r'_{02} \\ r'_{10} & r'_{11} & r'_{12} \\ r'_{20} & r'_{21} & r'_{22} \end{pmatrix} = \begin{pmatrix} 1 & 0 & 0 \\ 0 & 1 & 0 \\ 0 & 0 & 1 \end{pmatrix} \quad \text{equation (13)}$$

As described, the position $P_0$ in the first coordinate system $(X_0Y_0Z_0)$ of the magnetic field generation apparatus 7 is converted to the position $P_2$ of the second coordinate system $(X_2Y_2Z_2)$ on the basis (origin) of the center $O_2$ of the 3D image M3 according to equation (5) and equation (11). The direction $V_0$ in the first coordinate system $(X_0Y_0Z_0)$ is converted to the direction $V_2$ of the second coordinate system $(X_2Y_2Z_2)$ according to the following equation (14).

$$V_2 = R_{12}R_{01}V_0 \quad (14)$$

FIG. 4 shows the 3D image M3 indicating a situation that the insertion portion 2b of the endoscope 2 is inserted into the bladder B. A position of the inner wall surface of the sphere (inner wall surface of the bladder B) where the visual line direction V intersects from the position of the viewpoint Pv of the objective optical system 10 can also be handled by using the second coordinate system $(X_2Y_2Z_2)$.

The center $O_2$ as the origin of the second coordinate system $(X_2Y_2Z_2)$ is a position of a midpoint of a line segment connecting a neck PR that is the entrance to the bladder B and an opposing site PT of the neck PR. The second coordinate system $(X_2Y_2Z_2)$ is set such that a left side wall side in the bladder B is the $X_2$ direction, a right side wall side is a $-X_2$ direction, a front wall (belly) side of the patient P is the $Z_2$ direction, and a back wall (back) side of the patient P is a $-Z_2$ direction.

The 2D model image M2 shown in FIG. 3A and the like is obtained by developing or projecting the 3D image (inner wall surface of the bladder B approximated by the 3D image) shown in FIG. 4 along a plane including $X_2$ and $Y_2$.

Figure 5:
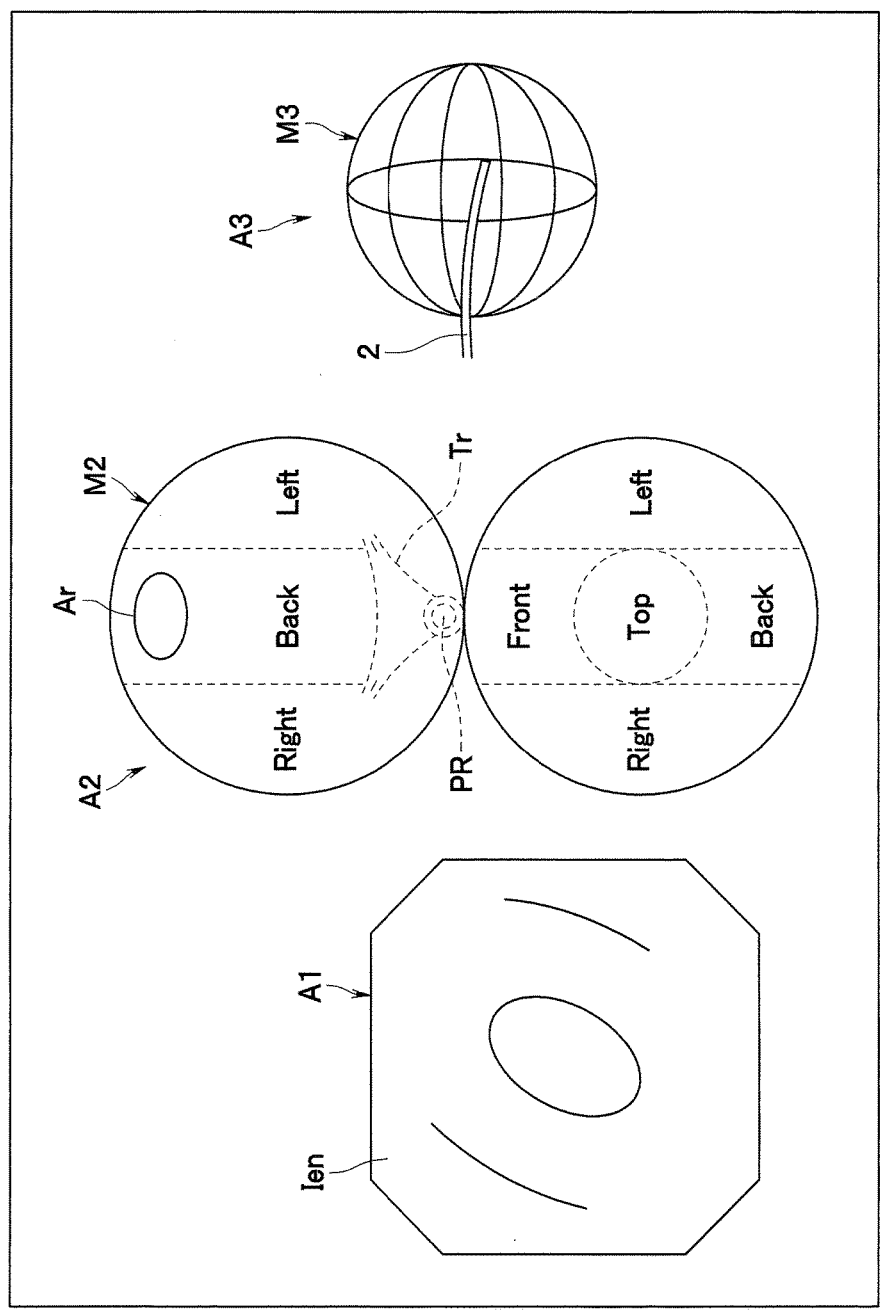
FIG. 5 is a diagram of a case in which an endoscopic image, the 2D model image, and the 3D image are displayed on a monitor at the same time.

FIG. 5 shows images displayed on the monitor 6 in a state that the release operation is not performed. An endoscope image Ien is displayed in a leftmost endoscopic image display area A1 in FIG. 5. The 2D model image M2 in the state that the release operation is not performed is displayed in a 2D model image display area A2 on the right side of the endoscopic image display area A1. The 3D image is displayed in a 3D image display area A3 on the right side of the 2D model image display area A2.

In FIG. 5, the 2D model image M2 shows the neck PR that is a representative region, a top portion (Top), a left side wall (Left), a right side wall (Right), a front wall (Front), and a back wall (Back) corresponding to the neck PR, and a trigone (Tr) indicating the neck PR and left and right urinary tracts. In FIG. 5, the region Ar (back wall part as indicated in the 2D model image M2) currently imaged (observed) by the endoscope 2 may also be displayed on the 2D model image M2, for example.

When the position of the viewpoint Pv and the visual line direction V in the second coordinate system $(X_2Y_2Z_2)$ of the objective optical system 10 of the distal end portion 2d are determined as shown in FIG. 4, a position Ps that is a coordinate position on the inner wall surface of the sphere (indicating the bladder B) formed at a center position of an image pickup surface 11a of the image pickup device 11 is obtained as follows by using a radius R of the sphere. A coefficient k satisfying the following equation (15) and equation (16) is calculated to obtain the position Ps in the second coordinate system $(X_2Y_2Z_2)$.

$$Ps = Pv + kV \quad \text{equation (15)}$$

$$|Ps| = R \quad \text{equation (16)}$$

The position calculation circuit 21c uses equation (15) and equation (16) to calculate the position Ps of the inner wall in the visual line direction V at each viewpoint Pv. When the position Ps is calculated, the distance calculation circuit 21a calculates |Pv−Ps| to calculate a distance (information) from the viewpoint Pv to the inner wall.

Although the shape of the bladder B is the sphere of the radius R (value of R is a predetermined value), the operator may bring the distal end portion 2d into contact with the inner wall (for example, top portion) of the bladder with a maximum distance from the entrance of the bladder to set the value of the radius of the sphere, for example.

The memory 22 shown in FIG. 2 is formed by using a ROM, a RAM (random access memory), a flash memory, or the like. The memory 22 records (or stores) various processing programs executed by the CPU 21 and various data and records (stores) the endoscopic image when the release operation is performed. The memory 22 includes an endoscopic image information recording section (or an endoscopic image information storage section) 22a configured to record (store) the information of the endoscopic image generated by the image generation circuit 4a and imported to the inside of the image processing apparatus 5 through the image import circuit 24 and the position information and the visual line direction information acquired by the position direction acquisition circuit 25 when the release operation is performed.

The memory 22 also includes an association information recording section 22b configured to record the priority Pi forming the index reflecting a selectively used predetermined feature in association with the endoscopic image to be recorded based on the predetermined feature. The association information recording section 22b includes, for example, a table storage section 22c configured to store table data (also called a table) for setting, on the priorities, regions (indicating ranges of position) or sites in the bladder B as the predetermined features where a lesion is easily generated. Note that the association circuit 21f may include the table.

FIG. 6A shows content of the table stored in the table storage section 22c. When the inner wall of the bladder B is classified into a plurality of regions as shown in FIG. 6A, the trigone (region of the trigone) is set to the highest priority, and the top portion is set to the lowest priority. In this case, the numbers indicate the priorities. The smaller the number is, the higher the priority becomes.

When the content of the table prioritizing the regions where a lesion is easily generated is used as a predetermined feature, images with indices reflecting the content of the table are generated.

Note that although FIG. 6A shows a case in which different priorities are allocated to respective names of the regions, regions of a same name may be sorted into a plurality of regions, and different priorities may be provided, for example. FIG. 6B shows an example in which regions with a name of back wall are sorted into a plurality of regions, and different priorities are provided.

Figure 6C:
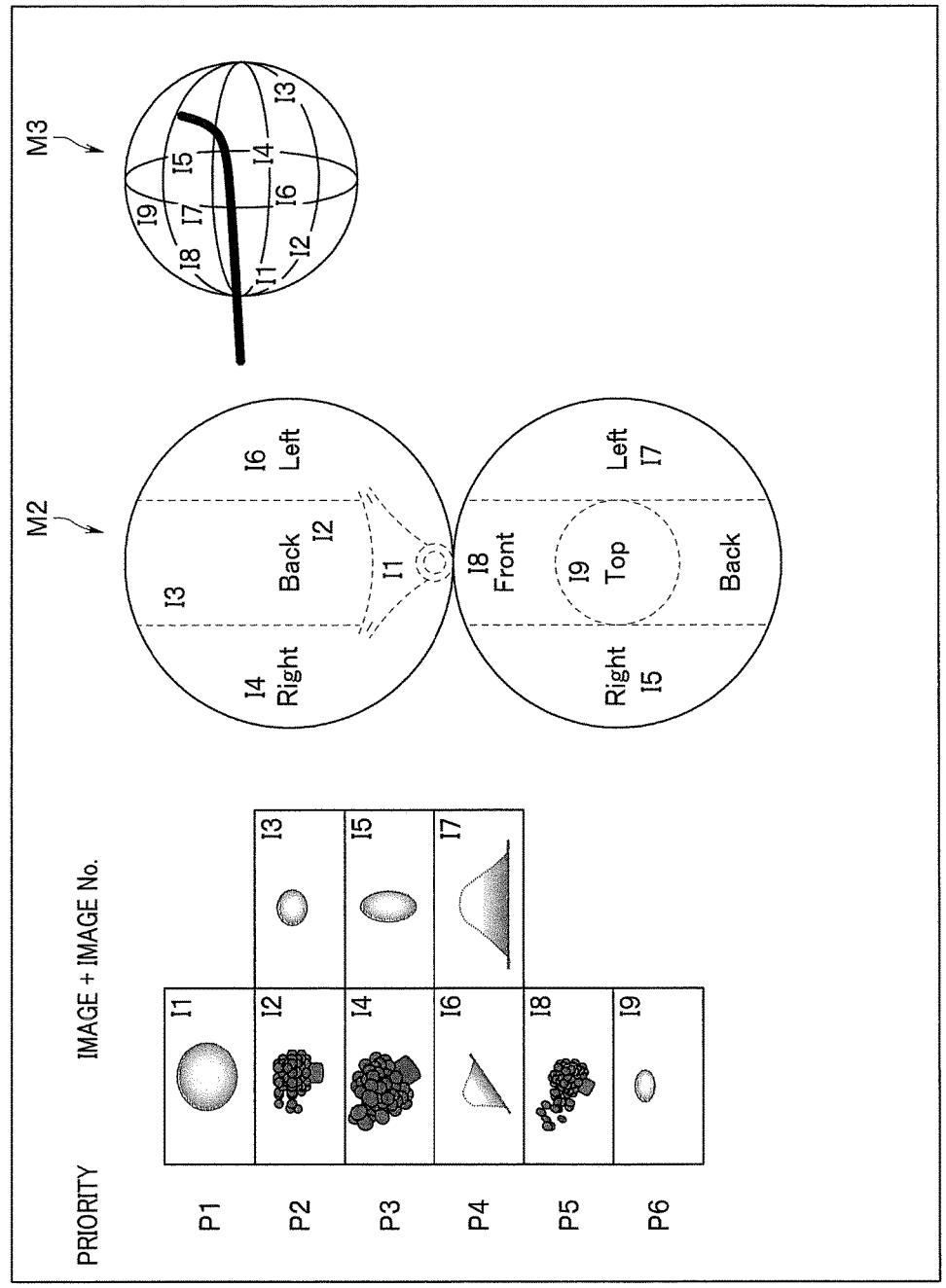
FIG. 6C is a diagram showing an association image provided with indices on the 2D model image and on the 3D image based on the priorities of lesion occurrence frequency (FIG. 6A)

In FIGS. 6A and 6B, a range of coordinates in each region is indicated for two or three regions with high priorities, and the range is not illustrated for regions with low priorities. As described later, the content of the table of FIG. 6A or 6B is used to generate images as shown in FIG. 6C.

A main feature of the present embodiment is that the image generation circuit 21e forming the image generation section generates images associating the indices and the position information of the inner wall on the 2D model image M2 or the 3D image based on a plurality of types of features or images acquired by the image acquisition section as described above.

Examples of the plurality of types of features include statistical features, such as lesion occurrence frequencies in the inner wall of the bladder B, and visual features, such as sizes of lesions and distances to the inner wall, or the indices are determined according to sizes of quantitative values obtained by quantifying the visual features.

The generated indices are symbols with regularity as described later, and the association circuit 21f or the index generation circuit 21b associates the order of size of the quantitative values with the symbols. The symbols may be provided again (corrected) based on the quantitative values of the corresponding observation sites (regions) according to the endoscopic images recorded (acquired) after the release.

The association information recording section 22b in the memory 22 records the association image shown in FIG. 3A. The bladder B can be approximated by the spherical three-dimensional (3D) image, and parameters, such as the radius, indicating the sphere are stored as the 3D image M3 in a patient image information storage section 22d in the memory 22. The image information of the 2D model image M2 obtained by developing the three-dimensional image of the bladder B as a luminal organ is also stored in the patient image information storage section 22d in the memory 22.

Therefore, the patient image information storage section 22d has a function of a 3D/2D image recording section 22e of the 3D image M3 and the 2D model image M2.

The 3D image M3 and the 2D model image M2 stored in the memory 22 are read out by, for example, the CPU 21 and are displayed on the monitor 6 through the display I/F 23. In this case, the 2D model image M2 and the 3D image M3 are displayed adjacent to the endoscopic image Ien, such as a movie, as shown in FIG. 5.

Note that although the 3D image M3 and the 2D model image M2 read from the patient image information storage section 22d are described here, the method of acquiring the 3D image M3 and the 2D model image M2 is not limited to this. For example, the 3D/2D image generation circuit 21d may use the observation position and the visual line direction data based on the endoscopic image Ien picked up by the image pickup section 12 to generate the 3D image M3 and the 2D model image M2 corresponding to the two-dimensional image data picked up (observed) by the image pickup section 12 of the endoscope 2.

In this case, the 3D/2D image generation circuit 21d may estimate a corresponding 3D shape from one two-dimensional image as in a method described in Japanese Patent No. 5354494 or a publicly known shape-from-shading method other than Japanese Patent No. 5354494, for example. A technique of estimating the 3D shape by combining a stereo method using two or more images, a three-dimensional shape estimation method based on monocular motion view, a SLAM method, and a position sensor may also be used. To estimate the 3D shape, 3D image data acquired from an external ultrasonogram acquisition apparatus, such as a CT apparatus, may be referenced to construct 3D shape data.

When the release operation is performed, the endoscopic image is recorded in association with the index according to the selected selection information. When instruction operation of an image reproduction switch 30b of the input device 30 or an image reproduction switch (not shown) provided on the endoscope 2 is performed for example, the image generation circuit 21e displays the images as shown in FIG. 3A.

The image import circuit 24 shown in FIG. 2 has a function of an image acquisition section configured to execute a process of importing (or acquiring) the endoscopic images generated by the processor 4 at a constant cycle. The image import circuit 24 acquires, for example, 30 endoscopic images per second that is the same as a frame rate, from the processor 4. The image import circuit 24 also receives the release signal from the processor 4.

The position direction acquisition circuit 25 controls the drive circuit 27 configured to drive the magnetic field generation apparatus 7 and causes the magnetic field generation apparatus 7 to generate a predetermined magnetic field. The magnetic sensor 13 detects the magnetic field, and the position direction acquisition circuit 25 generates, in real time, data of position coordinates (x, y, z) as the viewpoint of the objective optical system 10 and an orientation as the visual line direction (that is, Euler angle ($\psi$, $\theta$, $\phi$)), that is, the position information of the viewpoint and the visual line direction information, in the first coordinate system $(X_0Y_0Z_0)$ from a detection signal of the detected magnetic field. That is, the position direction acquisition circuit 25 configures an information acquisition section that acquires the position information and the direction information from the magnetic sensor 13 to acquire the position information of the viewpoint of the objective optical system 10 and the visual line direction information (also simply called position and visual line direction information).

The CPU 21 may store, in the memory 22, coordinate information obtained by converting the endoscopic image (information of the endoscopic image) imported by the image import circuit 24 and the position direction information calculated from the position direction information detected by the position direction acquisition circuit 25 (for example, after conversion to the second coordinate system $(X_2Y_2Z_2)$ on the basis of the center $O_2$ of the sphere by the coordinate conversion circuit 21g). Note that the information may be stored in the memory 22 without the conversion to the second coordinate system $(X_2Y_2Z_2)$.

The memory 22 records, in the association information recording section 22b, association information associating the endoscopic image imported by the image import circuit 24 and the position direction information when the endoscope image is imported.

In the present embodiment, the input device 30 includes, for example, a selection switch 30a for selecting a desired item from a plurality of prepared items for generating indices. The surgeon can operate the selection switch 30a to select an item reflecting a feature desired by the surgeon from the plurality of items for generating the indices reflecting a plurality (of types) of prepared features. Note that the index generation circuit 21b may be able to generate an index reflecting an inputted feature as the surgeon inputs a desired feature from the input device 30. That is, an index reflecting the feature may be able to be generated for a feature not prepared in advance, and an association image associating the index and the position information may be able to be generated. Note that although the CPU 21 configures the distance calculation circuit 21a, the index generation circuit 21b, the 3D/2D image generation circuit 21d, the image generation circuit 21e, the coordinate conversion circuit 21g, and the like in FIG. 2, hardware, such as electronic circuits, may be used to configure the circuits.

The medical apparatus 1 of the present embodiment includes: the patient image information storage section 22d (or the memory 22) forming a storage section configured to record information indicating a shape of a predetermined luminal organ; the position direction acquisition circuit 25 (the information acquisition section 25a of the position direction acquisition circuit 25) forming an information acquisition section configured to acquire position information and visual line information of a predetermined viewpoint provided in the predetermined luminal organ; the image import circuit 24 forming an image acquisition section configured to acquire an image obtained by observing inside of the predetermined luminal organ from the predetermined viewpoint; the alignment circuit 21h forming an alignment section configured to integrate the position information and the visual line information into a coordinate system of the shape of the predetermined luminal organ; the position calculation circuit 21c forming a position calculation section configured to calculate position information of an inner wall of the predetermined luminal organ opposing in the visual line direction from the predetermined viewpoint based on the position information and the visual line information integrated with the shape of the predetermined luminal organ by the alignment section; the index generation circuit 21b forming an index generation section configured to generate an index defined based on a predetermined feature in the inner wall; the association circuit 21f forming an association section configured to associate the index generated by the index generation section with the image acquired by the image acquisition section; and the image generation circuit 21e forming an image generation section configured to generate an image associating the index and the position information of the inner wall on a three-dimensional image of the predetermined luminal organ or on a two-dimensional model image obtained by developing the predetermined luminal organ.

Figure 7:
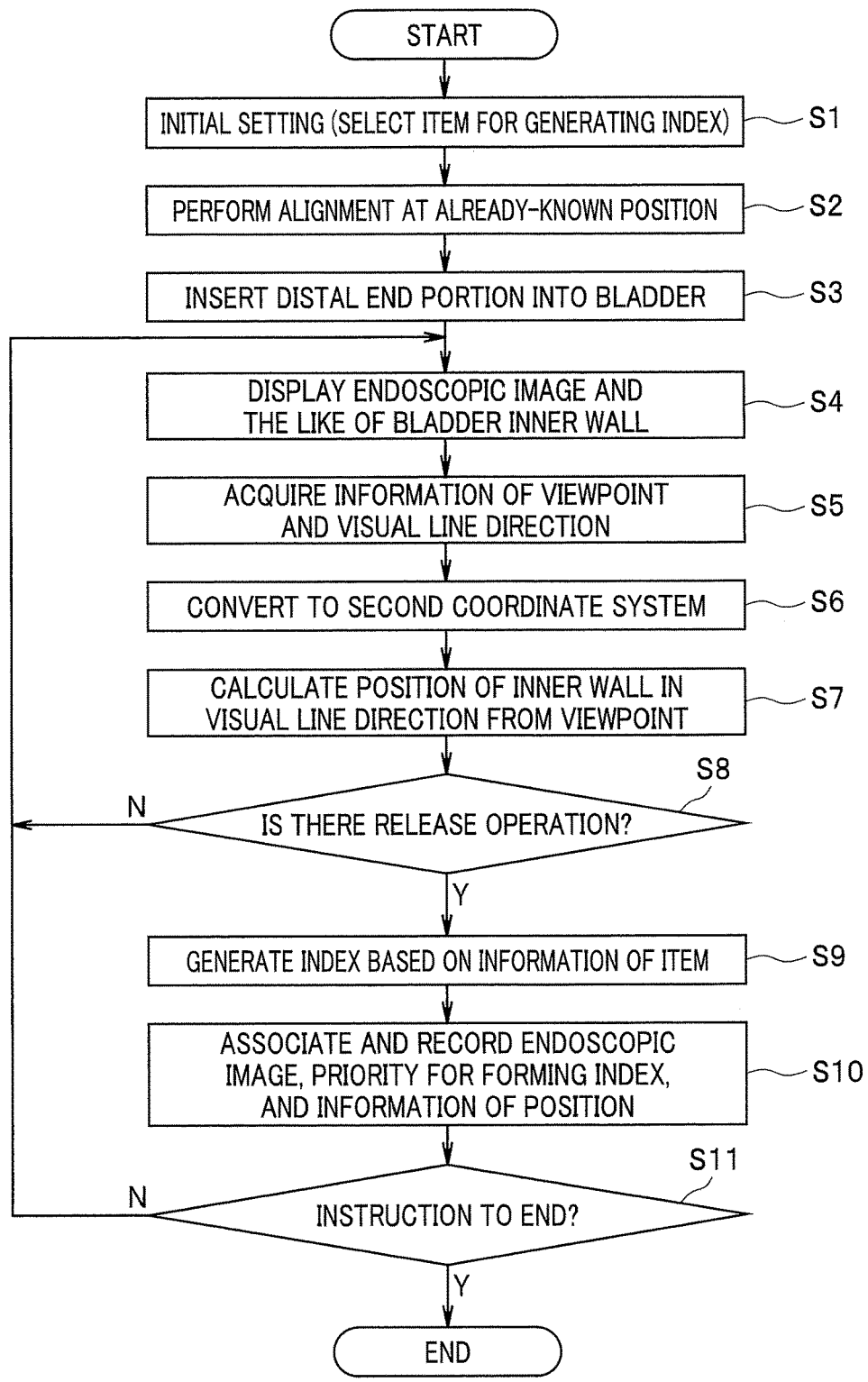
FIG. 7 is a flowchart showing operation in observation in the first embodiment.

Next, operation in the observation of the present embodiment will be described with reference to a flowchart of FIG. 7.

When the medical apparatus 1 enters an operation state, the surgeon performs initial setting in first step S1. The surgeon selects, from the input device 30, an index generation item for generating an index indicating the order of priority or the like for checking an endoscopic image of a lesion part or the like after observation of the inside of the bladder B and recording of the endoscopic image. It is mainly assumed in the following example that an item for generating an index of priority corresponding to a lesion occurrence frequency is selected.

In next step S2, the surgeon inserts the endoscope 2 into the urethra of the patient P and performs alignment of coordinate systems at an already-known position. Since the position information and the visual line direction information acquired by the position direction acquisition circuit 25 for the magnetic sensor 13 of the distal end portion 2d is information under the first coordinate system $(X_0Y_0Z_0)$, alignment with the second coordinate system $(X_2Y_2Z_2)$ used in the bladder B is performed. Alignment of the first coordinate system and the intermediate coordinate system here is performed by obtaining the position and direction information of the entrance of the bladder. Alignment of the intermediate coordinate system and the second coordinate system is performed by obtaining the center position of the bladder. The position direction acquisition circuit 25 chronologically acquires the position information and the visual line direction information of the distal end portion through the magnetic sensor 13 of the distal end portion 2d.

In the present embodiment, the alignment of the first coordinate system $(X_0Y_0Z_0)$ and the intermediate coordinate system $(X_1Y_1Z_1)$ is performed, and the alignment of the intermediate coordinate system $(X_1Y_1Z_1)$ and the second coordinate system $(X_2Y_2Z_2)$ is further performed to perform the alignment of the first coordinate system $(X_0Y_0Z_0)$ and the second coordinate system $(X_2Y_2Z_2)$. In this way, the position information and the visual line direction information acquired by the position direction acquisition circuit 25 are converted to the position information and the visual line direction information in the second coordinate system $(X_2Y_2Z_2)$ by the coordinate conversion circuit 21g.

In next step S3, the surgeon inserts the distal end portion 2d of the endoscope 2 into the bladder B. As shown in step S4, the monitor 6 displays the endoscopic image when the inner wall of the bladder B is observed (imaged) as shown for example in FIG. 5 and displays the 2D model image M2 and the 3D image M3. However, at this stage, the position and the visual line direction of the endoscope 2 are not displayed on the 3D image M3 (the position and the visual line direction of the endoscope 2 are determined on the 3D image M3 after a process of step S5 and subsequent steps, and the position of image pickup on the 2D model image M2 is also determined). Therefore, only the endoscopic image may be displayed as an example of display of FIG. 5.

In next step S5, the position direction acquisition circuit 25 acquires the information of the viewpoint and the visual line direction of the objective optical system 10 of the distal end portion 2d in the bladder B. As shown in step S6, the coordinate conversion circuit 21g converts the information to information of the viewpoint and the visual line direction in the second coordinate system $(X_2Y_2Z_2)$.

In next step S7, the position calculation circuit 21c calculates the position (position Ps of FIG. 4) of the inner wall of the bladder B in the visual line direction (equation (15) and equation (16) described above). Note that a distance L from the viewpoint to the inner wall (position on the inner wall) may also be calculated.

In next step S8, the CPU 21 determines whether release operation is performed. When the release operation is performed, the index generation circuit 21b in next step S9 generates, based on the information of the item, an index including information of the order of priority (priory) for the endoscopic image when the release operation is performed. More specifically, for the endoscopic image to be recorded by the release operation, the index generation circuit 21b generates an index indicating the priority for defining (or determining) the order of reproduction in reproducing the endoscopic image for checking and the position (information) of the inner wall of the endoscopic image to be recorded. Note that the judgement of the release operation in step S8 may be performed between steps S3 and S4. In other words, the position of the inner wall of the bladder B in the visual line direction from the viewpoint may be calculated after the release operation is performed.

In next step S10, the memory 22 (the association information recording section 22b of the memory 22) associates and records the endoscopic image, the information of priority, and the position information. Note that although the order of priority is generated every time the image is acquired in the processing example of FIG. 7, the order of priority may be provided after the completion of the entire image acquisition. Alternatively, a temporary order of priority may be generated (determined) every time the image is acquired, and a final order of priority may be performed after the completion of the entire image acquisition.

In next step S11, the CPU 21 judges whether an instruction for ending the observation is inputted from, for example, the input device 30. If the instruction is not inputted, the CPU 21 returns to the process of step S4. If the instruction is inputted, the CPU 21 ends the process of FIG. 7. If the release operation is not performed in step S8, the CPU 21 moves to the process of step S4.

In this way, when the inner wall of the bladder B is observed, and the surgeon performs the release operation, the endoscopic image at the timing of the release operation is recorded in the memory 22. The information of the priority is generated based on the information on the basis of the position of the inner wall, and these (endoscopic image, position information, and information of priority) are associated and recorded in the memory 22.

Figure 8A:
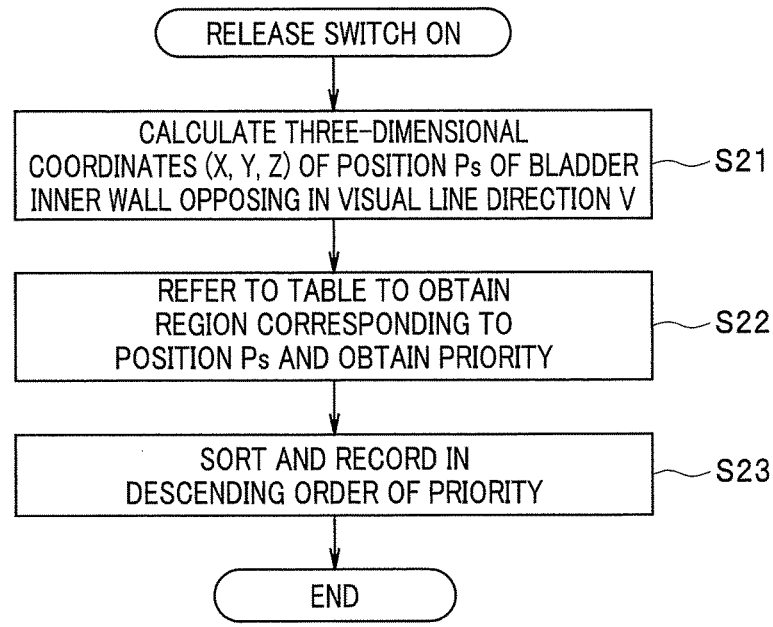
FIG. 8A is a flowchart showing a process of generating the indices for setting the priorities according to the content of the table when release operation is performed.
Figure 8B:
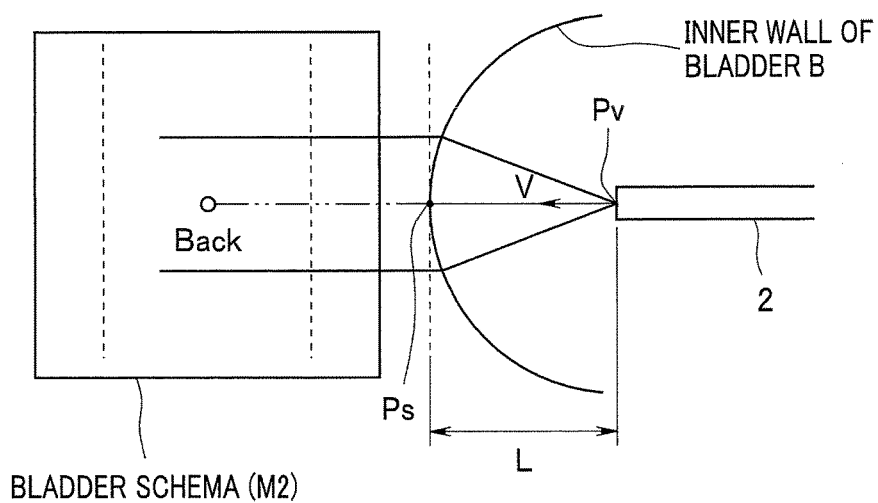
FIG. 8B is an explanatory diagram of operation of FIG. 8A.

FIG. 8A shows a processing example when an item for generating an index of priority corresponding to the lesion occurrence frequency is selected. FIG. 8B shows an explanatory diagram of operation of the process.

FIG. 8B shows a situation of observing the back wall of the inner wall of the bladder B after the distal end portion 2d of the endoscope 2 is inserted into the bladder B and shows a correspondence between a back wall part of the bladder B and a part equivalent to the back wall of the bladder schema. FIG. 8B shows a situation of observing a region around the position Ps of the inner wall in the visual line direction V from the viewpoint Pv (of the objective optical system 10) in the distal end portion 2d and shows part of the bladder schema corresponding to the observed region on the left side.

When the release switch 14 is turned on, the position calculation circuit 21c calculates (in the second coordinate system ($X_2Y_2Z_2$)) a three-dimensional position (X, Y, Z) of the position Ps of the bladder inner wall opposing in the visual line direction V from the viewpoint Pv in first step S21.

In next step S22, the index generation circuit 21b refers to the table of FIG. 6A or FIG. 6B to obtain a region corresponding to (or including) the position Ps and obtains the priority when the position Ps corresponds to the region. When the position Ps is a region in the back wall (Back) as shown for example in FIG. 8B, the position Ps corresponds to the priority of P2 with reference to FIG. 6A and corresponds to the priority of P2 or P3 with reference to FIG. 6B.

In next step S23, when the release operation is performed at a plurality of positions, the positions are sorted in descending order of priority. The positions are recorded in the memory 22 along with the position information, and the process of FIG. 8A ends.

When the release operation is performed at a plurality of places in the inner wall of the bladder B in this way, the image generation circuit 21e generates, for example, an association image as shown in FIG. 6C, and the memory 22 records the generated association image. Note that although the positions of the endoscopic images recorded by providing the endoscopic images (thumbnail images of the endoscopic images) Ii are indicated on both images of the 2D model image M2 and the 3D image M3 in the association image of FIG. 6C, the positions of the endoscopic images recorded by providing the endoscopic images (thumbnail images of the endoscopic images) Ii may be indicated on one of the 2D model image M2 and the 3D image. In association images of FIG. 10 and subsequent drawings described later, the positions of the endoscopic images recorded by providing the endoscopic images (thumbnail images of the endoscopic images) Ii are indicated on the 2D model image M2, for example.

Figure 9A:
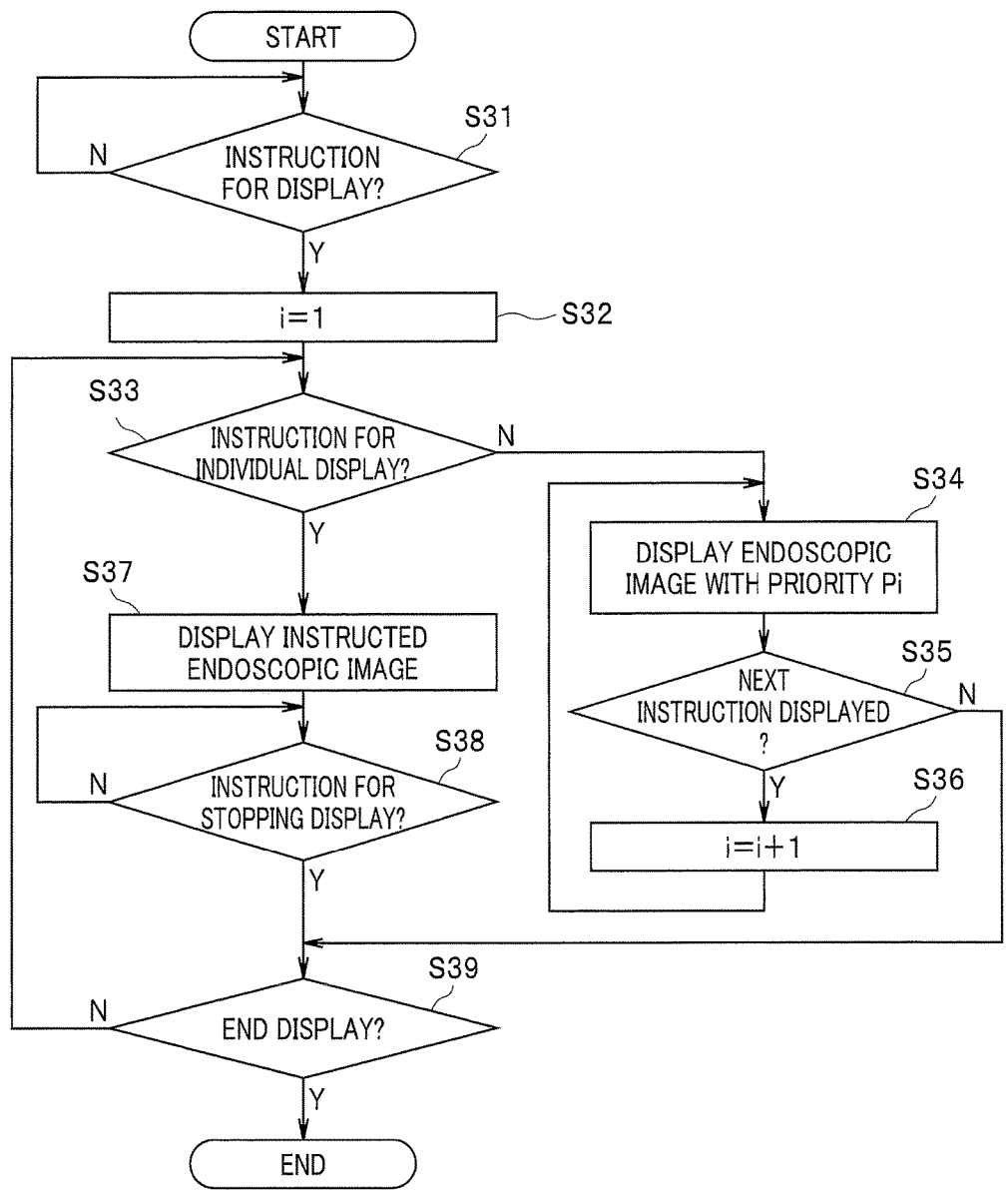
FIG. 9A is a flowchart showing a processing procedure in displaying recorded endoscopic images.

When the surgeon performs instruction operation for displaying (reproducing and displaying) the association image from the input device 30 or the like, the CPU 21 controls the monitor 6 to display the association image shown in FIG. 6C. FIG. 9A shows a process of displaying the association image.

In first step S31, the CPU 21 waits for input of an instruction for displaying the association image from the input device 30 or the like. When an instruction is inputted, the CPU 21 sets a parameter i of the priority Pi to 1 in next step S32.

In next step S33, the CPU 21 judges whether there is an instruction for individually displaying the endoscopic images from the input device 30 or the like. Although the surgeon can check the recorded endoscopic images according to the order of priority, the surgeon can select to individually display the endoscopic images according to the intention of the surgeon independently from the order of priority.

Figure 9B:
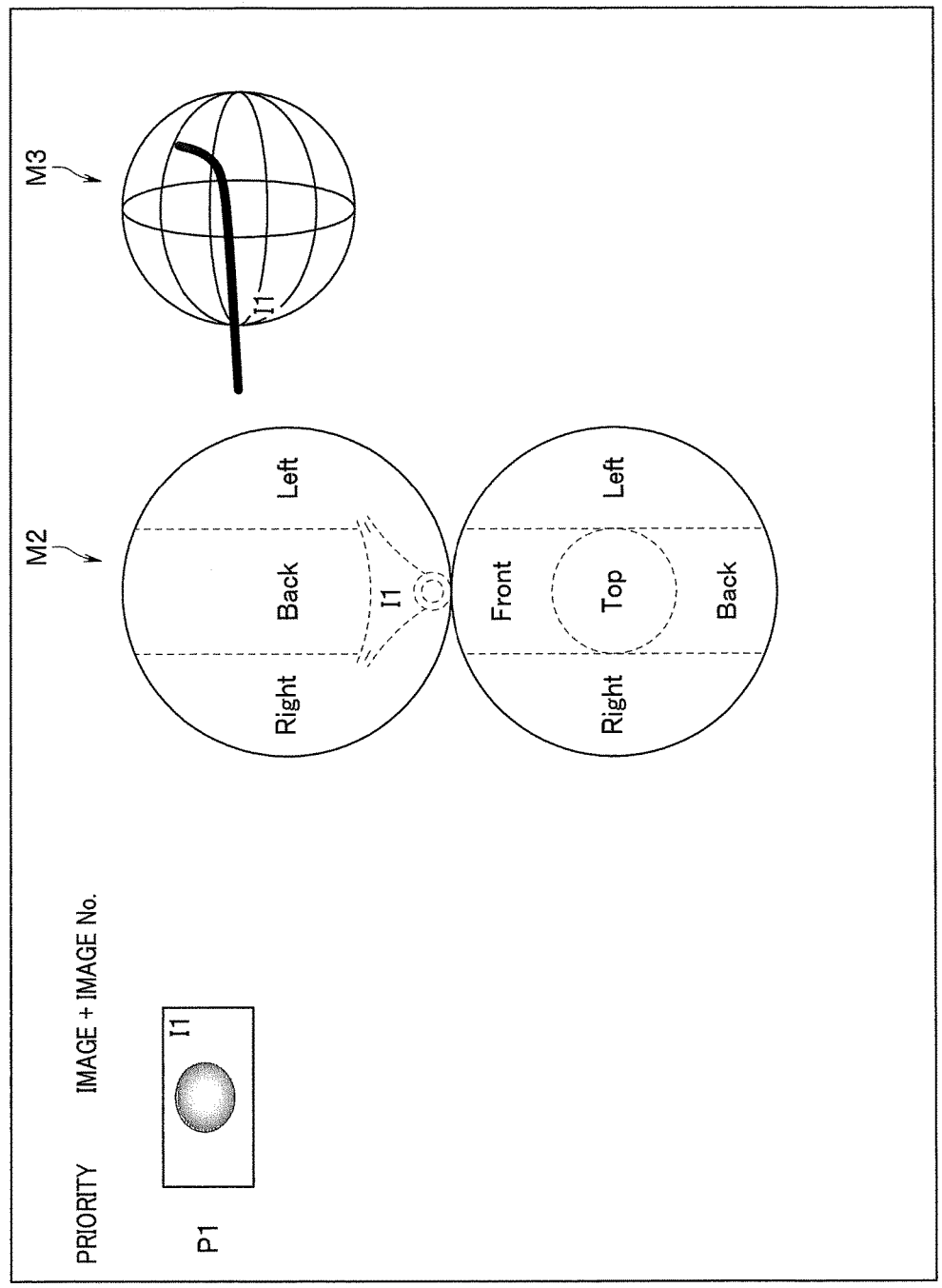
FIG. 9B is a diagram showing an association image provided with an index on the 2D model image and on the 3D image (corresponding to a priority P1)

When a judgement result indicates that there is no instruction for individually displaying the endoscopic images, the CPU 21 performs control to display the endoscopic image with the currently highest priority Pi (that is, endoscopic image of the site with the highest lesion occurrence frequency) in next step S34. At the present time, the endoscopic image with the priority Pi (i=1) with i=1 is displayed on the monitor 6. The image in this case is, for example, as shown in FIG. 9B. Other than FIG. 9B, a display mode of displaying the 2D model image M2 and the 3D image M3 on the right side of the endoscopic image with the priority Pi (i=1) along with the endoscopic image is possible as shown in FIG. 3B, or only the endoscopic image with the priority Pi (i=1) may be displayed as shown in FIG. 3C.

Figure 9C:
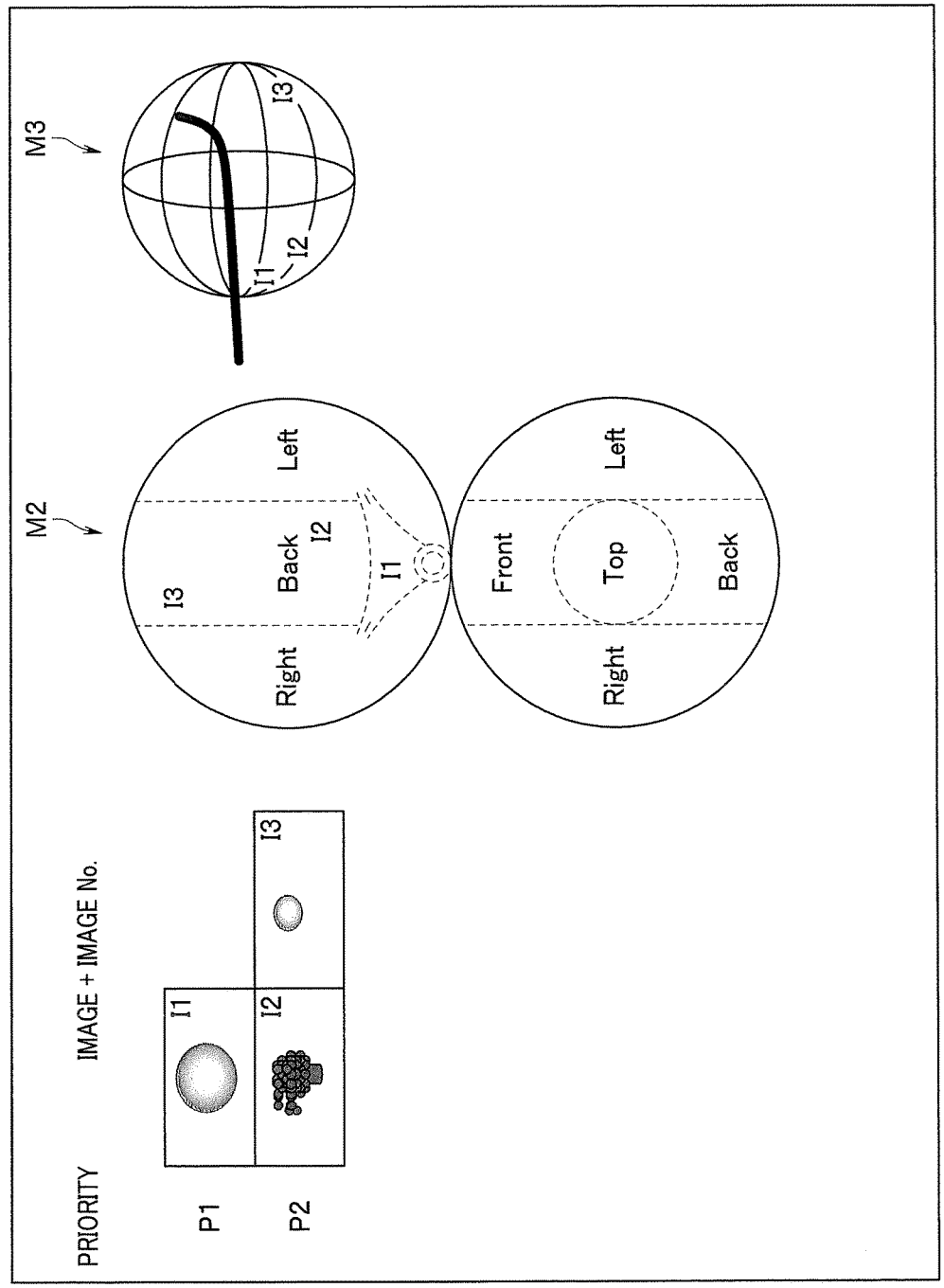
FIG. 9C is a diagram showing an association image provided with indices on the 2D model image and on the 3D image (corresponding to the priority P1 and a priority P2)

In next step S35, the CPU 21 judges whether there is a display instruction for a next endoscopic image from the input device 30 or the like. If there is display instruction for the next endoscopic image, the CPU 21 increases i of the priority Pi by 1 in next step S36 and returns to the process of step S34. In this case, the endoscopic images with the second priority Pi (i=2) are displayed as shown in FIG. 9C or 9D. If there is no display instruction for the next endoscopic image in step S35, the CPU 21 moves to a process of step S39 without executing the process of step S36.

On the other hand, if there is an instruction for individually displaying the endoscopic images in step S33, the CPU 21 performs control to display the instructed endoscopic images in step S37 and proceeds to a process of next step S38. In step S38, the CPU 21 continues to display the instructed endoscopic images until an instruction for stopping the display of the instructed endoscopic images is inputted.

When an instruction for stopping is inputted, the CPU 21 judges whether an instruction for ending the display is inputted from the input device 30 or the like in step S39. If an instruction for ending the display is not inputted, the CPU 21 returns to the process of step S33. If an instruction for ending the display is inputted, the CPU 21 ends the process of FIG. 9A.

According to the operation, the endoscopic images reflecting the feature desired by the surgeon can be prioritized to sequentially check a plurality of endoscopic images, because the endoscopic images are recorded in association with the priorities according to the item for generating indices desired by the surgeon (in other words, according to content reflecting the feature desired by the surgeon). Therefore, the surgeon can efficiently check a plurality of endoscopic images that the surgeon desires to check. In the example described above, the surgeon can sequentially prioritize and check endoscopic images of the sites with high lesion occurrence frequencies.

Although the association image including the indices corresponding to the lesion occurrence frequency is generated when the lesion occurrence frequency as a feature in the inner wall of the bladder B is selected as an item for generating indices in the example of the operation described above, an item reflecting a feature with a type or content different from the lesion occurrence frequency can be selected. Hereinafter, a case in which an item for generating indices other than the item of the lesion occurrence frequency is selected from the input device 30 will be described.

When a plurality of endoscopic images are recorded in chronological order according to the order of release operation, and the surgeon selects an item for generating indices reflecting a feature for prioritizing the endoscopic images in the chronological order of recording, the table is not referenced in step S22 following step S21 in the process shown in FIG. 8A. The priorities are determined in the order of release operation, and information, such as priorities and positions, is recorded in the memory 22 in the order of release operation along with the endoscopic images. In this case, time periods of the release operation may be recorded, and the priorities may be determined from the time periods.

In this case, an association image as shown in FIG. 10 is generated, and the association image is recorded in the memory 22. When the order of release operation is defined as Ri, the priority Pi in FIG. 10 is the same as the order Ri of release operation. When the time period of the release operation is defined as Ti, and the time period Ti is used instead of the order Ri of release operation, the priority Pi is the same as the time period Ti of release operation (that is, as for the time period Ti of the release operation, a higher priority Pi is provided to a time period of the release operation performed temporally earlier).

Note that for the association images illustrated in FIG. 10 and subsequent drawings, the positions of the endoscopic images recorded with the image No. of the thumbnail images are indicated only on the 2D model image M2. The positions of the endoscopic images recorded with the image No. of the thumbnail images may also be indicated on the 3D image M3 as shown in FIG. 3A. The association image indicating the positions of the endoscopic images recorded with the image No. of the thumbnail images may be generated only on the 3D image M3.

FIG. 11 shows an example of an association image generated when an item for generating indices by prioritizing the size of lesion is selected. In this case, the predetermined feature is a visual feature, and the visual feature is also a geometric feature. As described below, a quantitative value generation section (or a quantitative value generation circuit) configured to quantify a geometric feature to generate a quantitative value is included.

Figure 12:
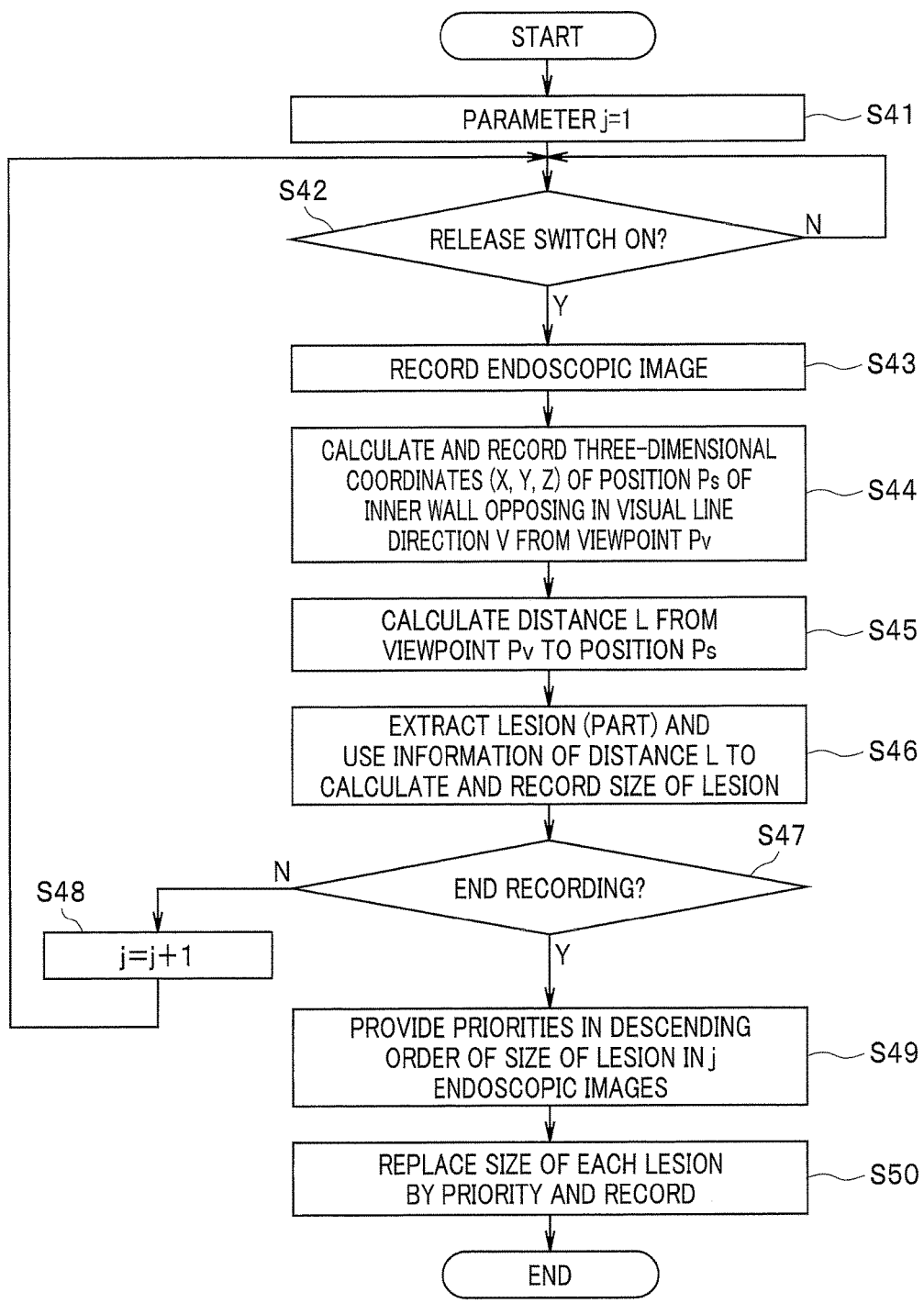
FIG. 12 is a flowchart showing a process of generating the indices of FIG. 11.

In this case, indices provided with the priorities Pi are generated in a process shown for example in FIG. 12. In first step S41, the CPU 21 sets a parameter j indicating the number of times of release operation to 1, and in next step S42, the CPU 21 waits until the release switch 14 for performing the release operation is turned on.

When the release switch 14 is turned on, the CPU 21 records the endoscopic image at the timing of the release in the memory 22 in next step S43. As shown in step S44, the CPU 21 calculates the three-dimensional coordinates (X, Y, Z) of the position Ps of the bladder inner wall opposing in the visual line direction V at the viewpoint Pv and also records the information of the calculated three-dimensional coordinates of the position Ps in association with the endoscopic image. As a result, the position of the recorded endoscopic image can be superimposed (added) on the 2D model image or on the 3D image.

As shown in step S45, the CPU 21 calculates the distance L from the viewpoint Pv to the position Ps. In other words, the distance calculation circuit 21a forming the quantitative value generation section sets the viewpoint as a predetermined quantification reference position (reference position of quantification) and calculates the distance L from the viewpoint to the position Ps on the inner wall as a quantitative value. Note that as described later, the urethra (neck) as a predetermined feature position in the bladder B may be set as a predetermined quantification reference position to generate an index, and an association image associating the index, the endoscopic image, and the like may be generated.

In next step S46, the CPU 21 extracts the lesion (part) in the endoscopic image and uses the information of the distance L to calculate the size of the lesion (part) forming the geometric feature. The CPU 21 records the size in association with the endoscopic image.

In next step S47, the CPU 21 judges whether an instruction for ending the recording based on the release operation is inputted. If the recording is not finished, the CPU 21 increases the parameter j by 1 in next step S48 and returns to the process of step S42. If an instruction for ending the recording is inputted, the CPU 21 provides priorities in descending order of the size of lesion in j times of recording of the endoscopic images in next step S49.

In next step S50, the CPU 21 replaces the information of the size recorded in association with the recorded endoscopic image by the information of the priority and records the information in the memory 22. The CPU 50 ends the process of FIG. 12. By executing the process, the image generation circuit 21e generates the association image shown in FIG. 11.

Although the association image as shown in FIG. 11 is generated in the process shown in FIG. 12, indices in which the order of the shape of the lesion as a geometric shape forming the geometric feature (more specifically, shape with high malignancy of lesion) is in the descending order of priority, instead of the size of the lesion forming the geometric feature, and an association image may be generated.

In this case, step S45 can be deleted, and steps S46, S49, and S50 can be changed to processing content corresponding to the shape of the lesion in FIG. 12, for example.

Indices in which coloring or colors (color features) of the lesion are in the descending order of priority, instead of the order of the shape of the lesion as a geometric shape forming the geometric feature (shape with high malignancy of lesion), and an association image may be generated. In this case, a process is executed, in which each pixel value in, for example, R, G, and B component images in the endoscopic image (also called observation image) recorded by releasing is extracted to calculate a quantitative value of the coloring feature in the endoscopic image.

Indices in which the priority increases with a decrease in the distance from the viewpoint to the inner wall when the release operation is performed may be generated (and an association image may be generated). In this case, an endoscopic image recorded closely at a short distance can include more information for the surgeon, and a high priority is set. In this case, the process of FIG. 12 can be more simplified, and the priorities can be provided to generate the indices and the like in the process.

Figure 13:
FIG. 13 is a diagram showing an association image when an ascending order of distance from a urethra is selected as an item for generating the indices.

FIG. 13 shows an example of an association image generated when an item for generating indices for prioritizing the small distance is selected (set) according to the distance from the urethra (neck) as a predetermined feature position to the position Ps of the inner wall.

The association image of FIG. 13 is obtained by setting the distance L in the process of FIG. 12 to a distance in which the viewpoint Pv is replaced by the urethra (neck) and providing the priorities in ascending order of distance.

Figure 14:
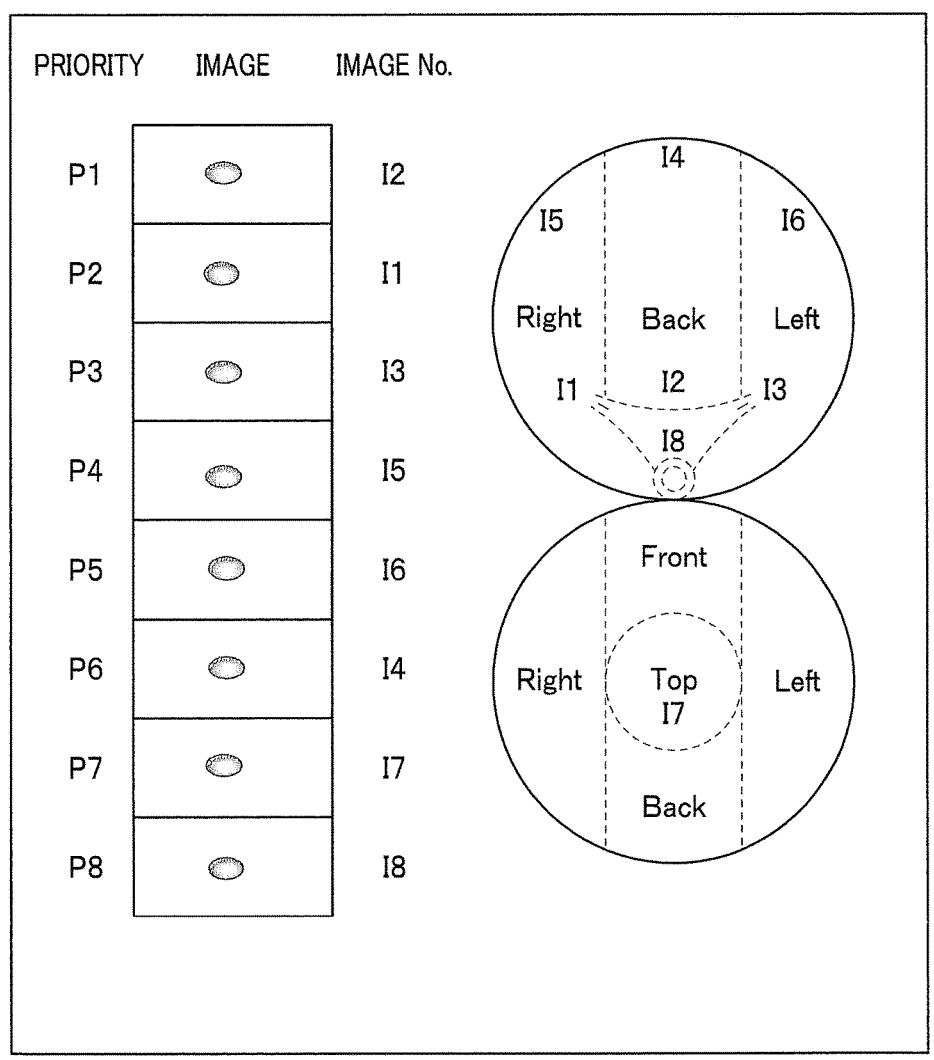
FIG. 14 is a diagram showing an association image when an order of location for performing random biopsy is selected as an item for generating the indices.
Figure 15:
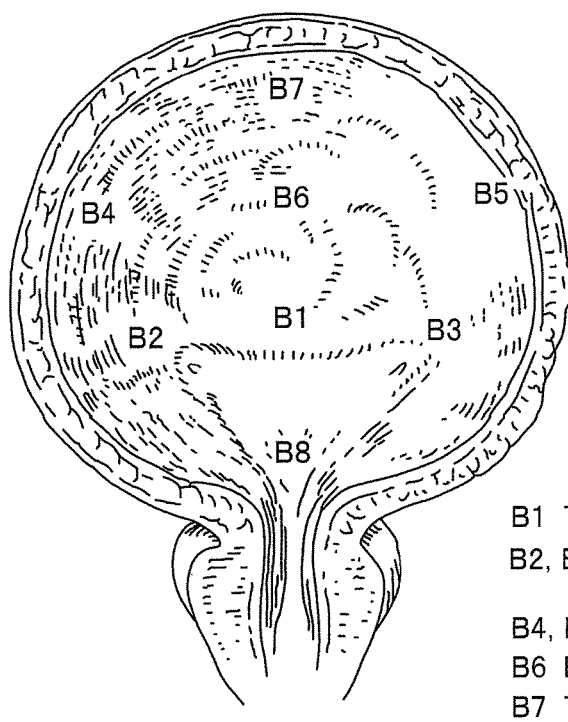
FIG. 15 is a diagram showing locations of random biopsy on an inner wall of the bladder.

FIG. 14 shows an example of an association image generated when an order of performing random biopsy inside of the bladder B is selected as an item for generating indices. In this case, an order Bi of performing random biopsy is the priority Pi. Note that FIG. 15 shows the order Bi of performing random biopsy in a cross-sectional view of the bladder B.

In addition, indices reflecting a feature (by selecting an item) according to the distance from a place operated in the past may be generated (and an association image may be generated).

When the endoscopic images are recorded in the normal light observation mode and the special light observation mode (narrow band light observation mode in a narrow sense), the indices may be generated (and an association image may be generated) by prioritizing the endoscopic images recorded in the special light observation mode.

Although the case of selecting one item or feature from a plurality of items or a plurality of features to generate the indices and the association image is mainly described in the example, a plurality of items or a plurality of features may be combined to generate the indices.

Figure 16:
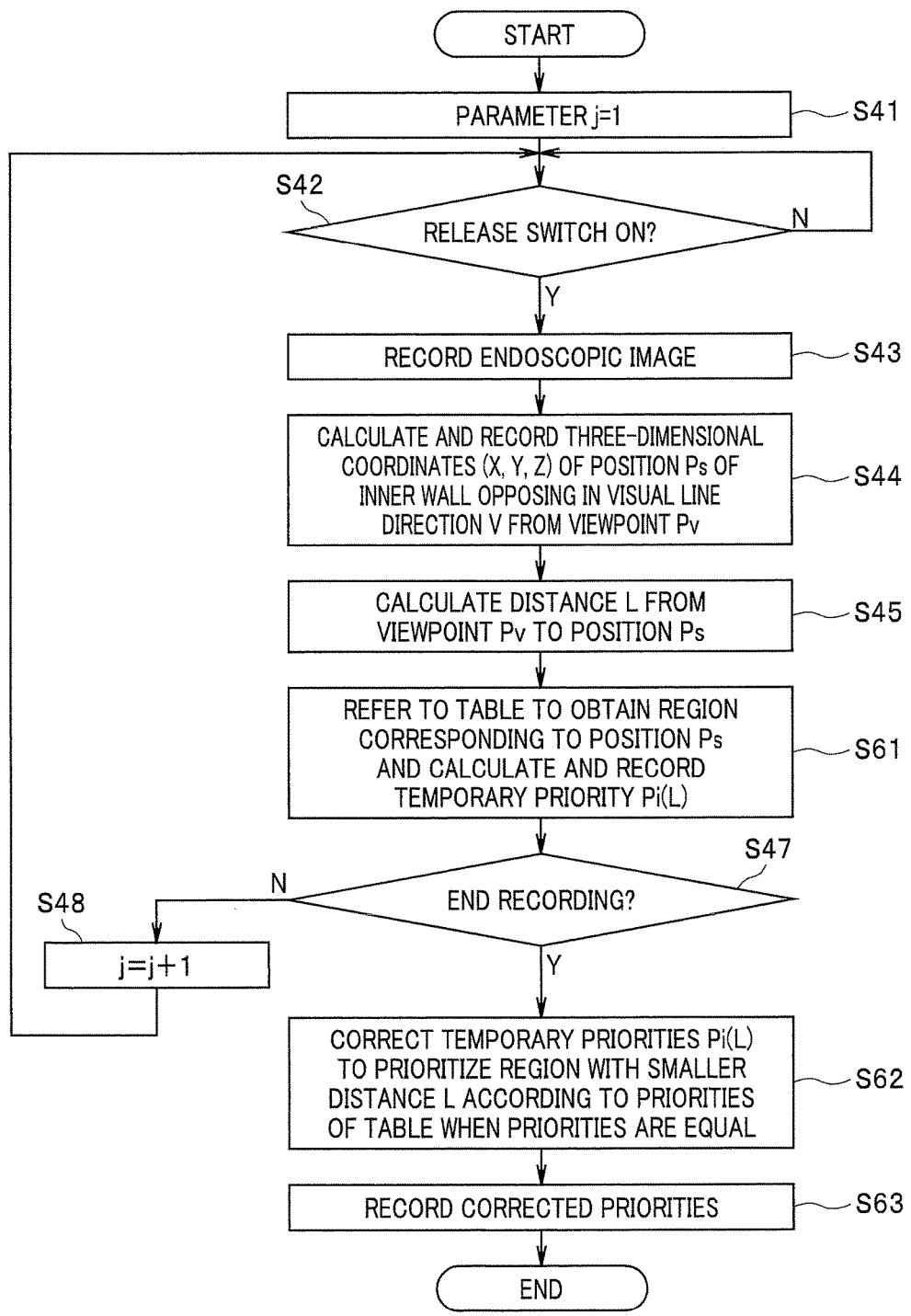
FIG. 16 is a flowchart showing a process of a modification of FIG. 8A.

FIG. 16 shows a process of generating the indices by taking into account the distance L from the viewpoint Pv in addition to the priorities in the table shown in FIG. 6A or 6B (priorities based on the feature of lesion occurrence frequency), for example.

The process in this case is a process in which part of the process of FIG. 12 is changed, for example. From step S41 to step S45 are the same as in the process of FIG. 12. The table is referenced as shown in step S61 following step S45, and the region corresponding to the position Ps is obtained. The priority Pi of the region is calculated as a temporary priority, and in this case, the information of the distance L is also added. For example, a temporary priority Pi(L) of the position Ps with the parameter j is added and recorded in the memory 22 in association with the endoscopic image. Next, the process of step S47 is executed. If the end of recording is not instructed, the process returns to step S43 through step S48.

On the other hand, if the end of recording is instructed, an order is provided to the temporary priority Pi(L) according to the order of sorting of the priorities in the table as shown in step S62. In this case, if the priorities are equal when the distance L is excluded, the priority with a smaller distance L is judged to be higher.

For example, when a region part included in the same region in the table of FIG. 6A or 6B is observed from different distances and recorded (for a plurality of times), the priorities determined by the table are calculated as the same priority. However, the priorities are corrected in the process of FIG. 16 such that the priority with a smaller distance is higher.

In next step S63, the priorities corrected in step S62 are recorded as final priorities in the memory 22 in association with the endoscopic images, and the process of FIG. 16 ends.

FIG. 17 shows an explanatory diagram of the operation of FIG. 16. In FIG. 17, the endoscopic images are recorded five times for example, and in this case, the endoscopic images are recorded for a plurality of times in regions with equal priorities in the table of FIG. 6A or 6B. In this case, the distance L is provided and recorded along with the priorities obtained from the table. When the priorities are equal, the priority with a smaller distance L is judged to have a higher priority for the final priority (rightmost section in FIG. 17). Note that as indicated in parentheses, numbers for providing the order may be further added to those with equal priorities to indicate the final priorities. For example, the priority of P2-2 is higher than P2-3 and lower than P2-1.

By executing the process of FIG. 16, the order of priority can be appropriately provided even when equal priorities are generated for the feature with only one item.

In this way, the present embodiment can provide a medical apparatus that can prioritize and check a plurality of images in the order desired by the surgeon.

According to the present embodiment, a feature can be selected from the items reflecting a plurality of features different from each other, and an association image provided with indices reflecting the selected feature can be generated. Therefore, a wide range can be handled even when the demand of the surgeon varies.

Furthermore, an association image provided with indices of a combination of a plurality of features can be generated, and a detailed demand of the surgeon can be handled.

Note that although one item is combined with an item related to the distance different from the item in the example described in FIGS. 16 and 17, the association image may be generated by appropriately combining two or three arbitrary items or features among the plurality of items or features.

Although the bladder B is spherical in the present embodiment, the shape of the bladder B may be an already-known shape, such as an ellipsoid and a cone.

Furthermore, images taken by an apparatus of CT, MRI, ultrasound, or the like may be used before the examination to acquire the shape of the inner wall of the bladder B.

What is claimed is:
1. A medical apparatus comprising:
a processor comprising hardware, wherein the processor is configured to:
  acquire position information and visual line information in an endoscope inserted into a predetermined organ;
  acquire an image obtained by observing inside of the predetermined organ from a predetermined viewpoint;
  convert the position information and the visual line information to a coordinate system of a model of the predetermined organ;
  calculate position information of an inner wall of the predetermined organ opposing in a visual line direction from the predetermined viewpoint based on the position information and the visual line information converted to the coordinate system of the model of the predetermined organ;
  generate an index indicating a priority corresponding to a lesion occurrence frequency of each of a plurality of regions obtained by classifying the inner wall into the plurality of regions based on the position information of the inner wall, when the image is acquired; and generate an image in which the index and position information of the inner wall are associated, for the image acquired.

2. The medical apparatus according to claim 1, further comprising:
an association section configured to associate the index generated by the index generation section with the image acquired by the image acquisition section, wherein
the image generation section generates an image in which the index and the position information of the inner wall are associated on a three-dimensional model image of the predetermined organ or a two-dimensional model image obtained by developing the predetermined organ.

3. The medical apparatus according to claim 2, wherein when a lesion occurrence frequency in the inner wall is designated as the predetermined feature, the association section associates a region divided according to the lesion occurrence frequency and the image acquired by the image acquisition section.

4. The medical apparatus according to claim 1, further comprising:
a distance calculation section configured to calculate a distance from a position of the predetermined viewpoint to a position of the inner wall calculated by the position calculation section.

5. The medical apparatus according to claim 1, wherein the index generation section generates the index with information of an order of priority based on the predetermined feature, for the image acquired by the image acquisition section.

6. The medical apparatus according to claim 5, further comprising:
a table data storage section configured to store table data provided with an order of priority that varies in each of a plurality of regions divided in advance in the inner wall based on the predetermined feature, wherein
the index generation section generates the index with the information of the order of priority according to which one of the regions in the table data includes the position information in the visual line direction in the image acquired by the image acquisition section.

7. The medical apparatus according to claim 5, further comprising:
an image recording section configured to record an observation image acquired by the image acquisition section when release operation is performed, wherein
the index generation section generates the index with the information of the order of priority based on the predetermined feature, for the observation image acquired by the image acquisition section when the release operation is performed, and
the image recording section records the index with the information of the order of priority in association with the observation image and information of a position on the inner wall of the predetermined organ where the observation image is acquired.

8. The medical apparatus according to claim 7, further comprising:
a control section configured to prioritize and read an observation image associated with an index in which the order of priority is high in the index with the information of the order of priority and to display the observation image on a display apparatus when reproduction of the observation image recorded in the image recording section is instructed.

9. The medical apparatus according to claim 7, further comprising:
a control section configured to prioritize and read the observation image in plurality associated with an index in which the order of priority is high and display the observation image in plurality on a display apparatus and to superimpose and display the index with the information of the order of priority associated with the observation image in plurality displayed on the display apparatus on a three-dimensional image of the predetermined organ or on a two-dimensional model image of the predetermined organ when reproduction of the observation image in plurality recorded in the image recording section is instructed.

10. The medical apparatus according to claim 7, wherein the predetermined feature for determining the index generated by the index generation section is a time period of acquisition of the observation image by the image recording section through the release operation.

11. The medical apparatus according to claim 1, further comprising:
an objective optical system configured to receive light from a subject to form an optical image of the subject; and
an alignment section configured to integrate, with a shape of the predetermined organ, position information and visual line information of the objective optical system acquired as the position information and the visual line information by the information acquisition section.

12. The medical apparatus according to claim 1, wherein when priorities corresponding to lesion frequency occurrences are same as each other in a plurality of images acquired, the processor is configured to correct each of the priorities of the plurality of images depending on a distance from the predetermined viewpoint to the inner wall, the distance being calculated for each of the plurality of images.

13. The medical apparatus according to claim 12, wherein the processor is configured to correct the priorities such that, in the plurality of images, the priority of the image, the distance calculated for which is relatively small, becomes relatively high.

14. A computer-readable storage device storing instructions that cause a computer to at least:
acquire position information and visual line information in an endoscope inserted into a predetermined organ;
acquire an image obtained by observing inside of the predetermined organ from a predetermined viewpoint;
convert the position information and the visual line information to a coordinate system of a model of the predetermined organ;
calculate position information of an inner wall of the predetermined organ opposing in a visual line direction from the predetermined viewpoint based on the position information and the visual line information converted to the coordinate system of the model of the predetermined organ;
generate an index indicating a priority corresponding to a lesion occurrence frequency of each of a plurality of regions obtained by classifying the inner wall into the plurality of regions based on the position information of the inner wall, when the image is acquired; and generate an image in which the index and position information of the inner wall are associated, for the image acquired.

* * * * *